(12) United States Patent
Blanch et al.

(10) Patent No.: US 6,263,558 B1
(45) Date of Patent: Jul. 24, 2001

(54) METHOD AND APPARATUS FOR FORMING DOUBLE-ARMED SUTURES

(75) Inventors: John F. Blanch, Tinton Falls, NJ (US); Timothy P. Lenihan, Morrisville, PA (US); David D. Demarest, Parsippany; William F. Smith, Ringoes, both of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/300,957

(22) Filed: Apr. 28, 1999

Related U.S. Application Data

(63) Continuation-in-part of application No. 08/845,638, filed on Apr. 30, 1997, now Pat. No. 5,937,504, and a continuation-in-part of application No. 08/804,477, filed on Feb. 21, 1997, now Pat. No. 6,058,821, and a continuation-in-part of application No. 08/803,573, filed on Feb. 21, 1997.

(51) Int. Cl.[7] .................................................. B23P 19/04
(52) U.S. Cl. ............................................. 29/517; 29/564.6
(58) Field of Search ........................ 29/517, 515, 564.1, 29/564.6, 705, 712, 711, 33 K, 33 R, 715; 198/391; 72/416; 83/170, 950, 153; 901/7

(56) References Cited

U.S. PATENT DOCUMENTS

| | | | |
|---|---|---|---|
| 4,072,041 | * | 2/1978 | Hoffman ................................ 72/416 |
| 5,226,336 | * | 7/1993 | Coates ..................................... 83/170 |
| 5,726,422 | * | 3/1998 | Haase et al. ......................... 83/153 X |
| 6,058,821 | * | 5/2000 | Demarest ............................. 83/950 X |
| 6,076,255 | * | 2/2000 | Shikakubo et al. ..................... 29/715 |

* cited by examiner

Primary Examiner—William Briggs
(74) Attorney, Agent, or Firm—Scully, Scott, Murphy & Presser

(57) ABSTRACT

A semi-automated machine for preparing double-armed sutures, i.e., a suture with a surgical needle at either end of the suture, from a bulk supply of surgical needles and an indefinite length of suture material is described. Each of the surgical needles has a suture receiving opening formed therein for receiving a suture. The machine includes a needle singulation station, a precise positioning station, a suture feeding and cutting station, a swage station, a pull-test station and an off-load station. A universal gripper mounted on a rotary indexing device automatically receives each individual needle in a predetermined orientation and conveys the needle for sequential processing from station to station to form the needle-suture assembly. A suture drawing and cutting station automatically inserts an end of the indefinite length of suture into the first of the pair of needles that form the double-armed suture. A swage station is provided for swaging the needle to close the suture receiving opening about the suture to secure said suture thereto. The suture drawing and cutting station then cuts the indefinite length, and inverts the cut end for insertion into the second of the pair of needles. The swage station then swages the second needle to close the suture receiving opening about the suture to secure said suture thereto and thereby form the double-armed suture.

30 Claims, 31 Drawing Sheets

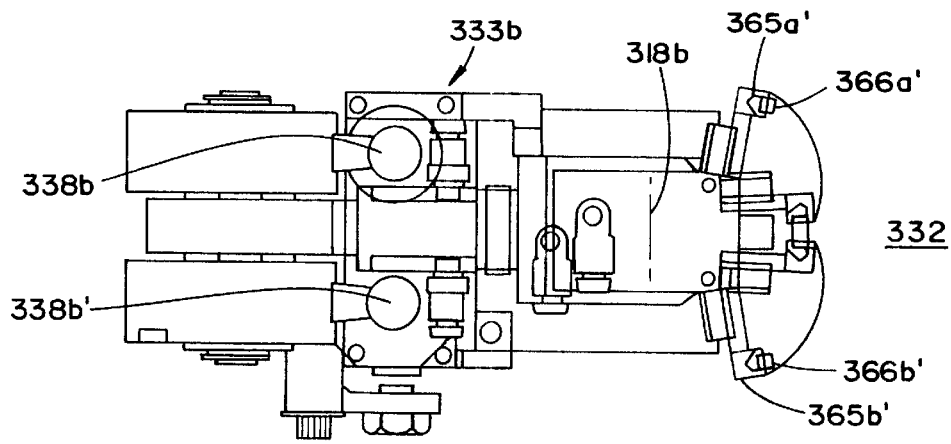
FIG. 11
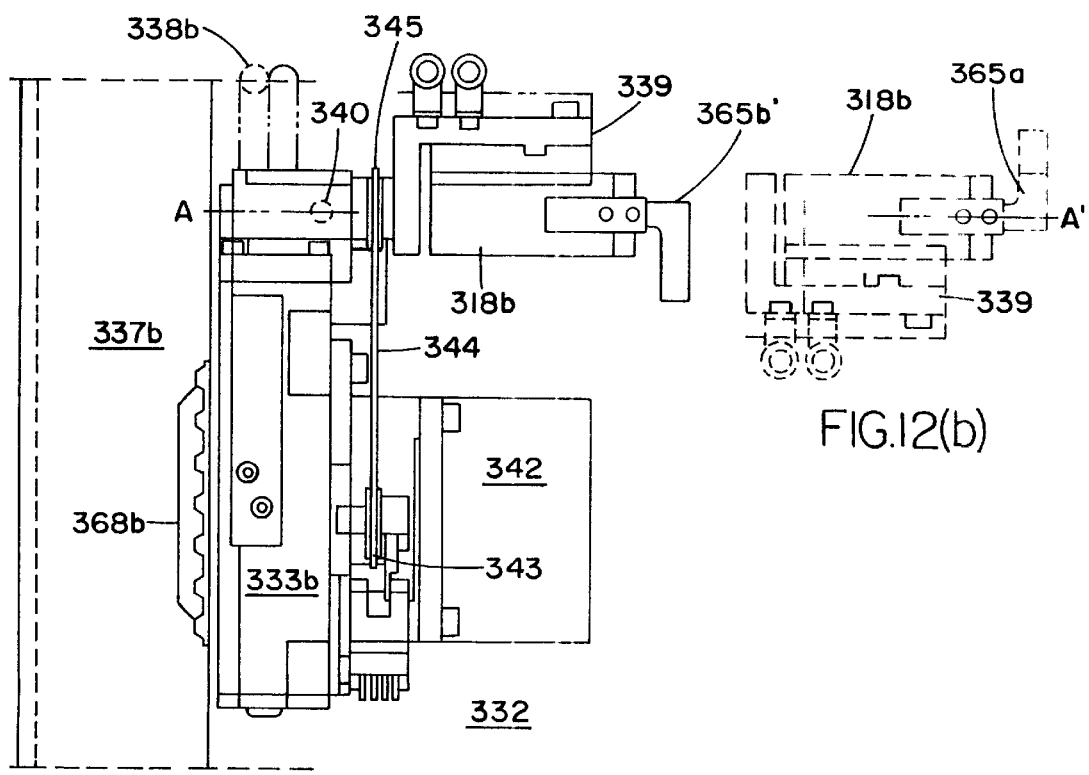
FIG. 12(b)
FIG. 12(a)

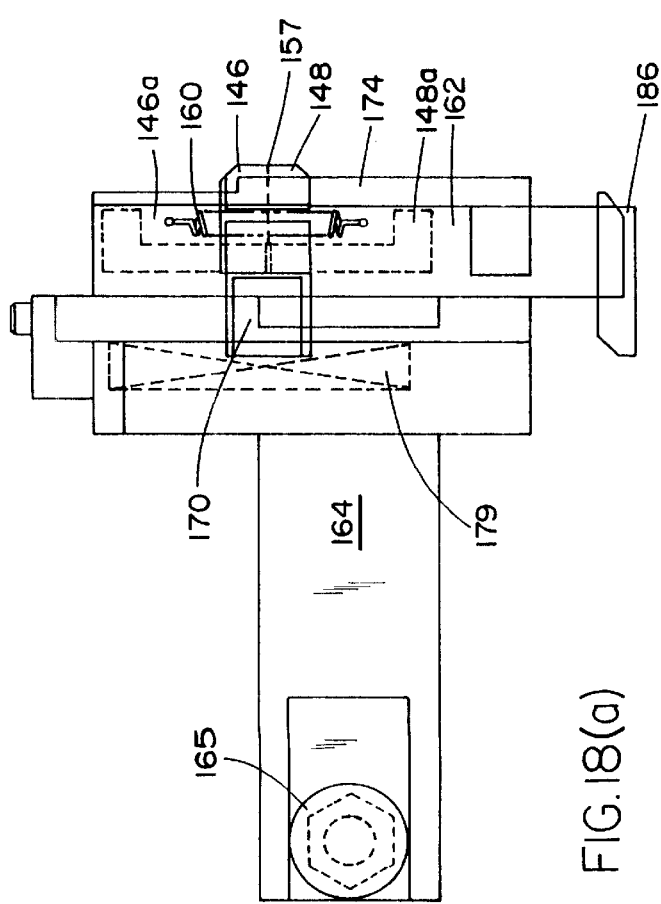
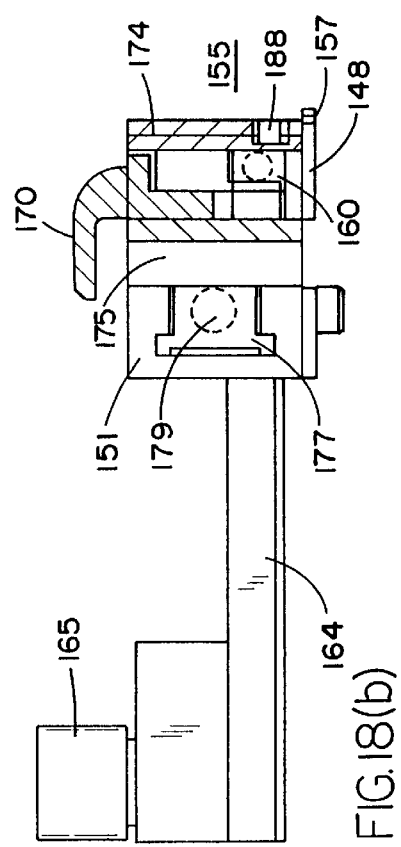
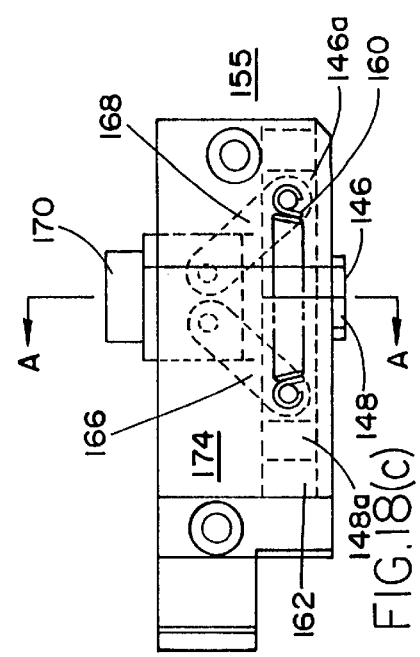
FIG.18(a)
FIG.18(b)
FIG.18(c)

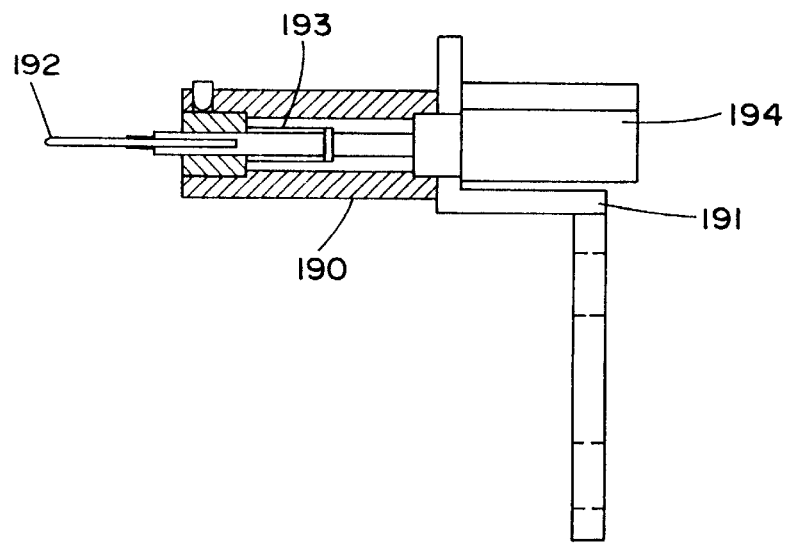
FIG.21
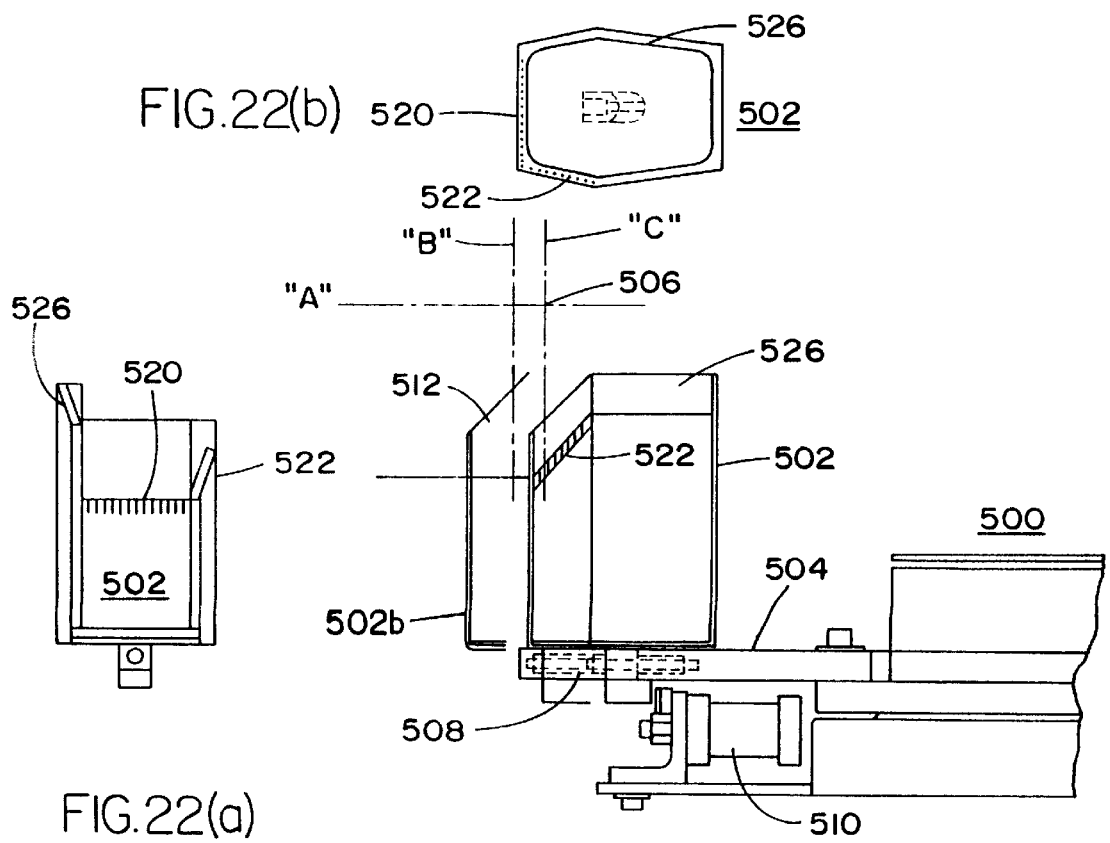
FIG.22(b)
FIG.22(a)
FIG.22

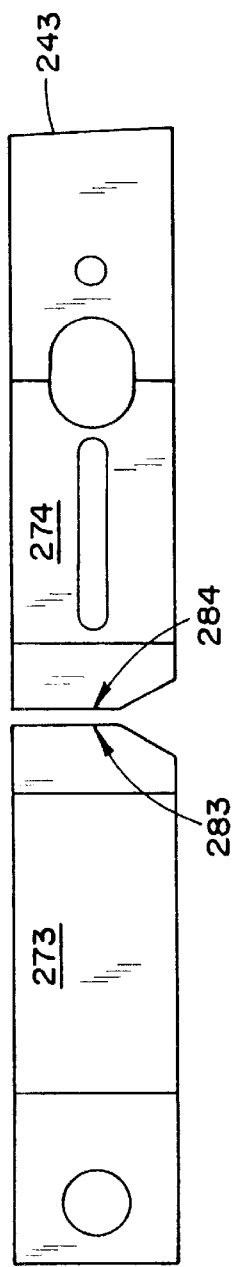
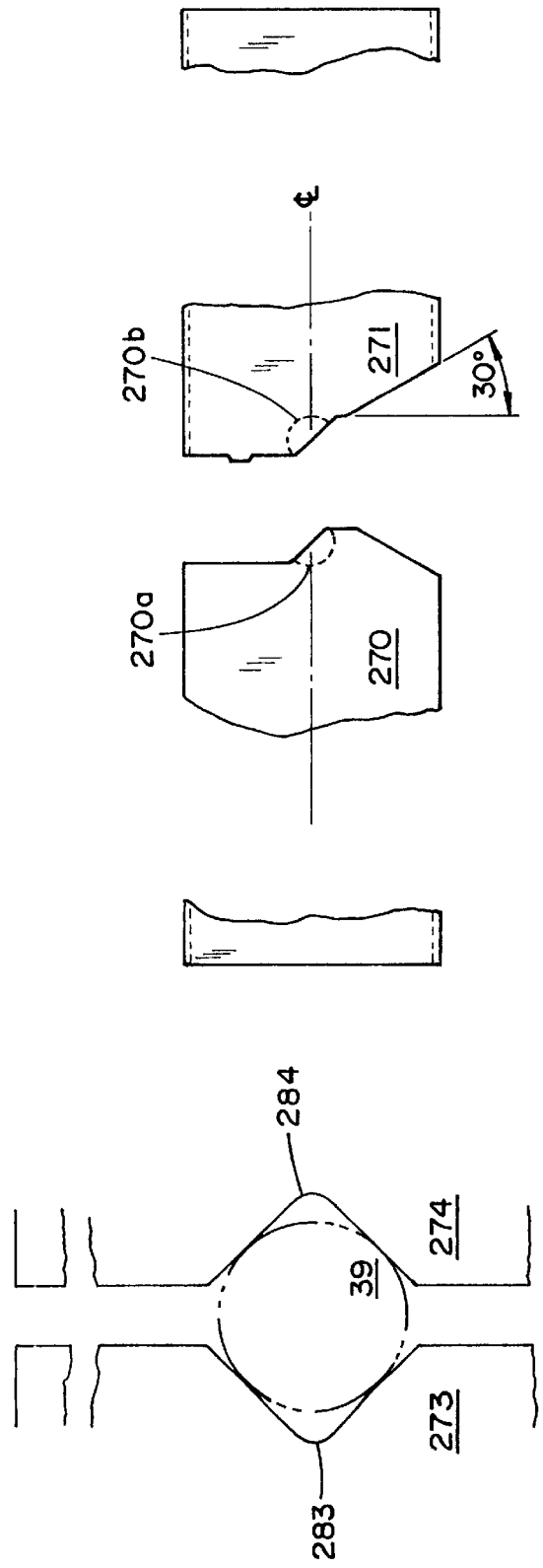
FIG.23(a)
FIG.23(b)
FIG.23(c)

US 6,263,558 B1

METHOD AND APPARATUS FOR FORMING DOUBLE-ARMED SUTURES

CROSS REFERENCE TO RELATED APPLICATIONS

This application is a Continuation-in-part of U.S. Ser. No. 08/845,638 filed on Apr. 30, 1997 now U.S Pat. No. 5,937,504 entitled STAND ALONE SWAGE DIAL; U.S. Ser. No. 08/804,477 filed Feb. 21, 1997, entitled "SUTURE CUTTING SYSTEM" now U. S. Pat. No. 6,058,821 and U.S. Ser. No. 08/803,573 filed Feb. 21, 1997, entitled "SUTURE CUTTING SYSTEM".

FIELD OF THE INVENTION

The present invention relates generally to machines for automatically swaging needles, such as surgical needles to a suture, and more specifically, to an apparatus that automatically swages, tests, and creates a double-armed suture, i.e., two needles having a single suture strand of predetermined length attached therebetween.

DESCRIPTION OF THE PRIOR ART

This application describes in detail an improvement of a portion of the apparatus disclosed in a series of U.S. Patents, of which U.S. Pat. No. 5,438,746 entitled "Needle Threading and Swaging System" is typical. All of the patents to this device are assigned to the assignee of the present invention.

The automatic needle and suture threading machine described in U.S. Pat. No. 5,438,746 is a highly automated machine intended for high volume production and packaging of needles and sutures wherein 20,000 to 40,000 needles and sutures are to be produced in a single run.

SUMMARY OF THE INVENTION

The present application describes an improved suture tower assembly for use with a swage dial assembly for the swaging of a pair of needles to a single suture, with the suture fed and cut to length by the suture tower apparatus to provide a double-armed suture, i.e. a suture with a surgical needle swaged each end of the suture.

The improved suture tower assembly of the present application includes an improved rotating or invertible suture gripper, an improved methodology to the suture cutting and insertion procedures, an improved cam dial, an improved universal needle gripper and an off set assembly that enables placement and retrieval of needles in a cut out die portion of a fixed swage die.

The present invention is also directed to improvements for a stand alone swage machine that is particularly adapted to enable subsequent automated handling of the needle, automatic swaging, automatic pull testing of the combined needle and suture (armed sutures), and bundling of the armed sutures for future packaging.

It is an object of the present invention to provide a machine which will efficiently handle small batches or production runs of double-armed sutures and to efficiently handle premium needles and super sharp cutting edge needles in an efficient manner without blunting the cutting edge of the needle, while bundling the same for future packaging.

It is another object of the present invention to provide a machine which is flexible in operation and enables quick changeovers between production lots and which minimizes the number of change parts required to migrate from one size needle or suture to another.

It is another object of the present invention to provide a machine which will handle odd runs or "doctors' specials" as they are referred to in the trade, where a particular surgeon expresses a preference for an unusual combination of needle type or size and suture material.

It is another object of the present invention to provide a plurality of universal gripper mounted on said swage dial for successively receiving an individual one of a plurality of precisely positioned needles at a first predetermined location and indexing each of said individual successive needles in a predetermined orientation from said first predetermined location through successive locations for sequential processing at subsequent predetermined locations, each of said universal grippers having a cam follower which cooperates with said cam dial to provide radial reciprocation of said universal grippers with respect to said swage dial in response to rotation of said cam dial.

It is another object of the present invention to provide an improved swage dial having an off set motion for the universal grippers that enables the grippers to place and retrieve needles held in a swage device having a swage die opening formed in a fixed swage die.

It is another object of the present invention to provide universal grippers which are rotated by said swage dial to each of said predetermined locations and reciprocated in and out of an operative position by said cam dial at each of said plurality of predetermined locations.

Finally, it is an object of this invention to provide a rotating array of needle collection buckets that enables collection of a predetermined number of needle and suture assemblies.

BRIEF DESCRIPTION OF THE DRAWINGS

FIG. 11 is an enlarged top plan view of the invertible suture clamp of the present invention, with the clamps illustrated in the open and closed positions.

FIG. 12(a) is an enlarged side elevation view of the invertible suture clamp illustrated in top plan view in FIG. 11, with the clamp in the inverted position.

FIG. 12(b) is an enlarged side elevation view of a portion of the invertible suture clamp illustrated in FIG. 12(a), with the clamp rotated to an insertion position.

FIG. 15(a) is detailed top view of the cam dial assembly 120 having cam dial plate 125 with cam follower 165a in a retracted position within cam track 160a.

FIG. 15(b) is cut away top view of the cam dial plate 125 showing cam follower 165a in an extended position within cam track 160a.

FIG. 18(a) is top plan view of the universal gripper and slide assembly used in the present invention, illustrating in dotted lines the various operating components thereof.

FIG. 18(b) is partially cross-sectioned side view of the universal gripper and slide assembly illustrated in FIG. 18(a).

FIG. 18(c) is a partially hidden front view of the universal gripper illustrated in FIG. 18(a) illustrating in dotted lines the actuating mechanism used to open the jaws of the universal gripper.

FIG. 21 is a partially cross section top view of the needle stripper assembly used in the present invention.

FIG. 22 is an elevation view of a needle bucket for the apparatus illustrating radial reciprocation of the needle bucket of the present invention.

FIG. 22(a) is a front view of the needle bucket for the apparatus illustrated in the elevation view of FIG. 22.

FIG. 22(b) is a top view of the needle bucket for the apparatus illustrated in the elevation view of FIG. 22.

FIG. 23(a) is a top plan view of the fixed and moveable swage dies of the present invention.

FIG. 23(b) is an enlarged view of a portion of the apparatus illustrated in FIG. 23(a) with a needle positioned therein before swaging.

FIG. 23(c) is a top plan view of portions of the suture guides of the present invention.

DETAILED DESCRIPTION OF THE PREFERRED EMBODIMENT

The present invention is directed to improvements in a stand alone swage machine that is particularly adapted to form double-armed sutures, that is, a suture with a surgical needle swaged to either end of the suture. This stand alone swage machine also provides semi-automated singulation of surgical needles to enable subsequent automated handling of the needle, provides automatic swaging of both needles, automatic pull testing of the combined needles and suture, and bundling for future packaging.

The present invention is directed to improvements in a stand alone swage machine that may swage a single needle to a single suture, i.e. an armed suture, or two needles to a single suture to form a double-armed suture, wherein the changeover may be accomplished through the control system, thereby avoiding time delays caused by part changes.

The present application describes improvements to one of the suture grippers to enable rotation of one the grippers, together with improvements in the operational methodology of the apparatus. The present invention enables the swaging of needles in symmetric dies, even when one of the dies is fixed in position.

This application describes in detail an improvement of a portion of the apparatus disclosed in U.S. Pat. No. 5,438,746 entitled "Needle Threading and Swaging System" assigned to the assignee of the present invention. The present invention includes an improved suture tower and drive train for the swage dial which is similar to the swage dial used in the machine described in the aforesaid patents.

The automatic needle and suture threading machine described in U.S. Pat. No. 5,438,746 is a highly automated machine intended for high volume production and packaging of needles and sutures wherein 20,000 to 40,000 needles and sutures are to be produced in a single run.

While the improvements to the suture tower and suture handling portions of this invention could be implemented in the completely automated device described in U.S. Pat. No. 5,438,746, the invention is described in the present application in the context of a machine designed to efficiently handle small batches or production runs on needles and to efficiently handle sutures having a pair of premium needles in an efficient manner.

The present invention is particularly adapted to form double-armed sutures intended for use in plastic surgery and cardiac surgery, which are typically very small needles having a radius of curvature of 0.188 to 0.219 inches, which are swaged to small diameter sutures having a diameter of 0.0035 to 0.0100 inches.

The present invention is also intended to handle odd runs or "doctors' specials" as referred to in the trade, where a particular surgeon expresses a preference for an unusual combination of needle type or size and suture material.

Figure 2:
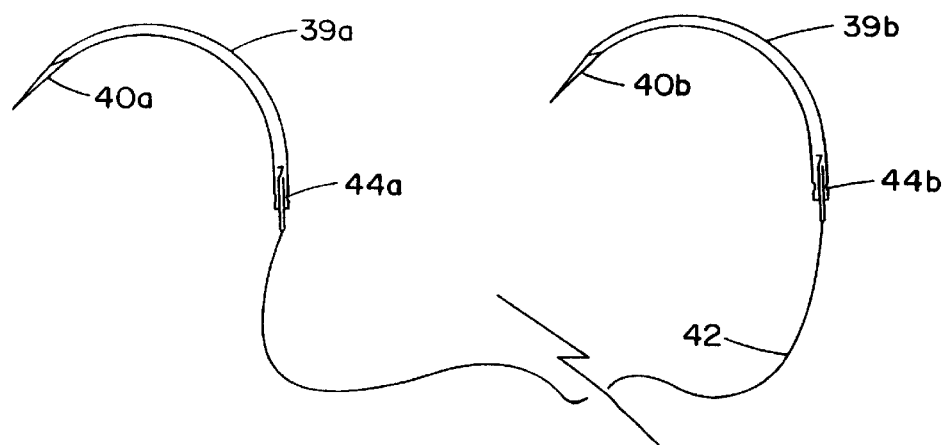
FIG. 2 is a diagrammatic view of an double-armed suture assembly having edged needles that are typical of the needles to be singulated and swaged according to the present invention.

The present invention minimizes the handling of the needle and is therefore particularly adapted for the automated handling of sutures having a pair of premium needles or cutting edge needles attached thereto such as the double-armed sutures illustrated in FIG. 2.

As illustrated in FIG. 2, the needles 39(a)(b) may include a ground or cutting edge portion 40(a)(b) and are illustrated with an attached suture 42 therebetween which has been attached to each needle by swaging as indicated at 44(a)(b). The suture 42 may be of any predefined length, but is commonly provided in lengths that are multiples of nine inches.

Generally, in the needle threading and swaging system of the present invention, parallel operations take place simultaneously at a plurality of different stations to ensure that approximately twenty to thirty (20–30) double-armed sutures (40 to 60 needles) are assembled and discharged per minute.

Figure 1:
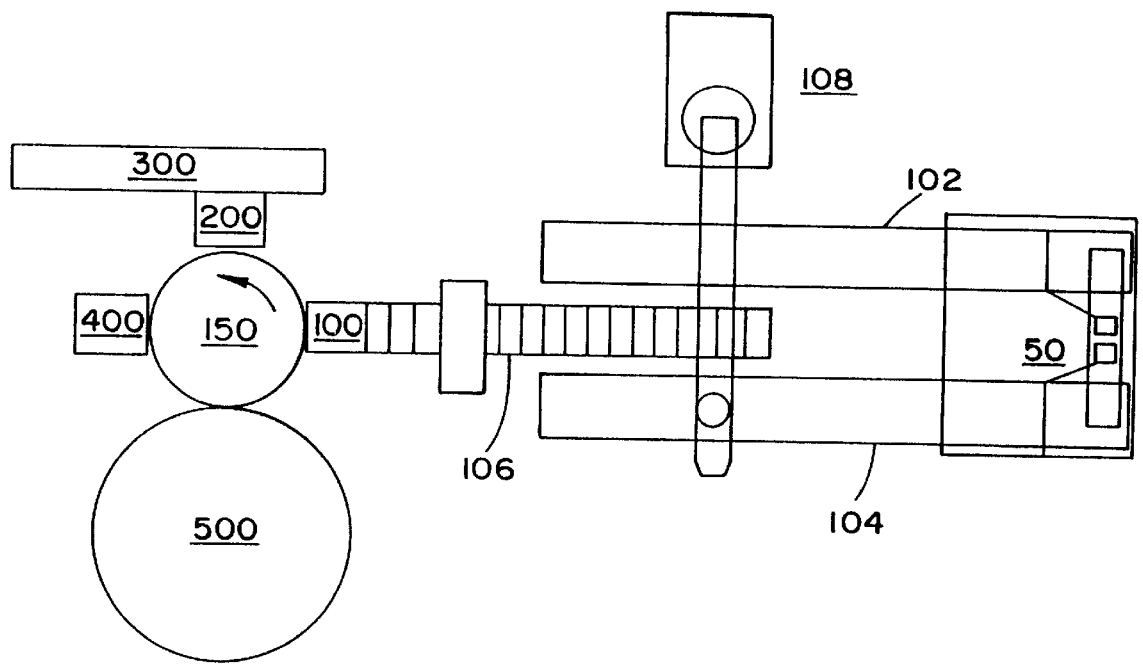
FIG. 1 is a diagrammatic top view of the needle threading and swaging system incorporating a semi-automatic needle sorting and singulating table for feeding individual needles to a universal gripper mounted on a rotary swage dial, an automatic swaging station, an automatic pull-test station, and an armed suture off-load and bundling station.

For instance, as shown in FIG. 1, a semi-automatic needle sorting and singulating station 50 assists an operator in sorting and singulating individual needles to a pair of translucent indexing conveyors 102,104 where the singulated needles are imaged by a vision system, selected by a computer, and transferred from the translucent indexing conveyors 102,104 to a precision indexing conveyor 106 by a robotic gripper 108. The precision indexing conveyor conveys precisely oriented surgical needles to a precise positioning station 100 to be sequentially received by a plurality of grippers mounted on the rotary swage dial 150. The rotary swage dial then rotates counter-clockwise as shown by the arrow in FIG. 1, to index each needle to the automatic swaging station 200 where the suture material is cut, inserted into the needle, and automatically swaged thereto. A suture drawing and cutting station 300 pulls, tips, cuts and inserts the suture into the needle to be swaged. In the double-armed suture process, the needle is swaged and then, the rotary swage dial 150 rotates to index the first needle of the suture to the automatic pull-test station 400 where each armed needle is pull-tested to ensure that the minimum and/or destructive pull-test requirements of the medical profession, are met. As the first needle of the pair is pull tested the second needle is swaged about the opposite end of the same suture by a unique invertible suture gripper that grips the tail end of the suture and inverts it into the second needle of the pair for swaging. Finally, the rotary swage dial indexes the pull-tested armed needle to the off-load station 500 while the second needle is pull tested. At the completion of the pull test, the first needle is ejected, the swage dial rotated, and the second needle ejected and handed off for suture bundling, or subsequent packaging at another location.

FIGS. 3(a) through 3(d) are block diagrams which illustrate the automatic needle threading and swaging process of the instant invention. For instance, at the needle singulating station 50, needles are first loaded onto a flat operator work surface at 10, singulated by the operator, and then automatically and individually fed at step 11 to one of the translucent indexing conveyors 102,104. The needles are imaged at step 12 and then evaluated with respect to orientation and position by a vision tracking system at step 13, picked up by a robot apparatus at step 14, transferred to a precision conveyor 106 for positioning by the robot apparatus 108 at step 15, and finally conveyed to a load station 100 where the needles are precisely positioned at step 16 and transferred to a universal gripper located on a rotary swage dial 150 for subsequent transfer to the swaging station 200 indicated at step 25. A detailed explanation of the apparatus used to carry out each step will be explained in further detail hereinbelow.

Figure 3A:
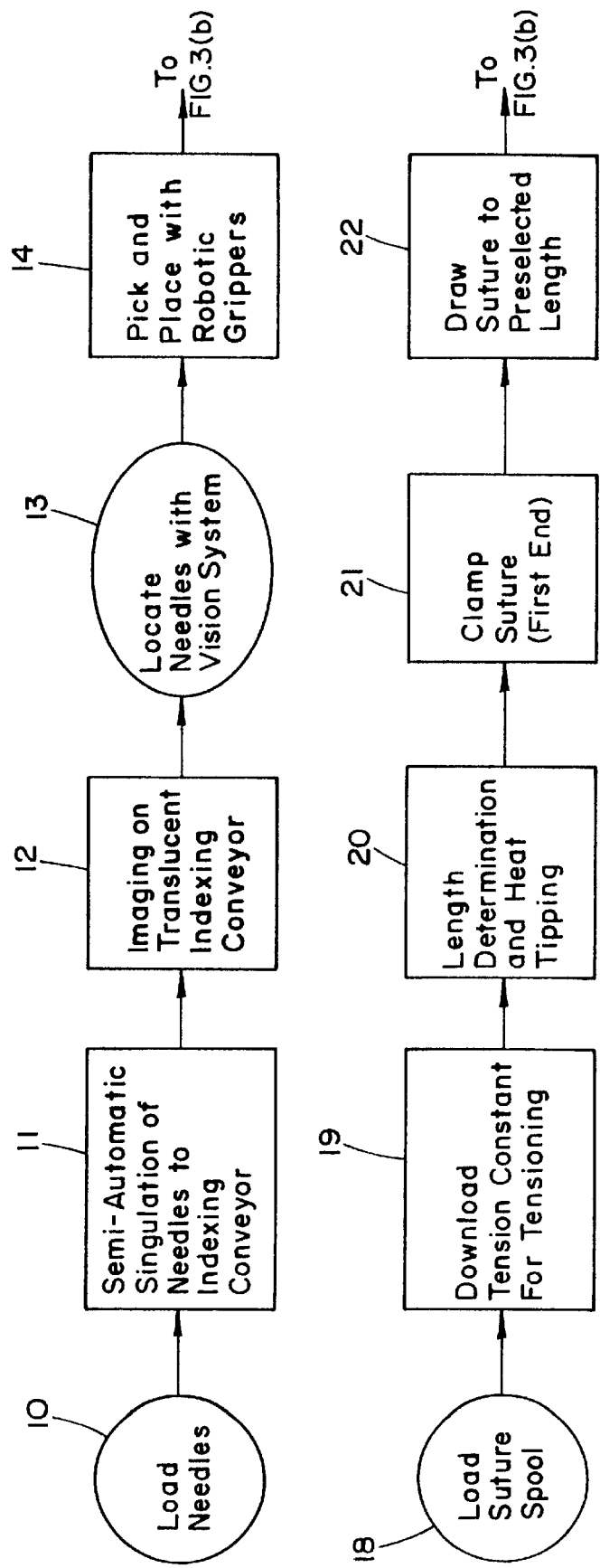
FIGS. 3(a)–3(d) together form a flow diagram illustrating the process for the needle threading and swaging system of the present invention.
Figure 3B:
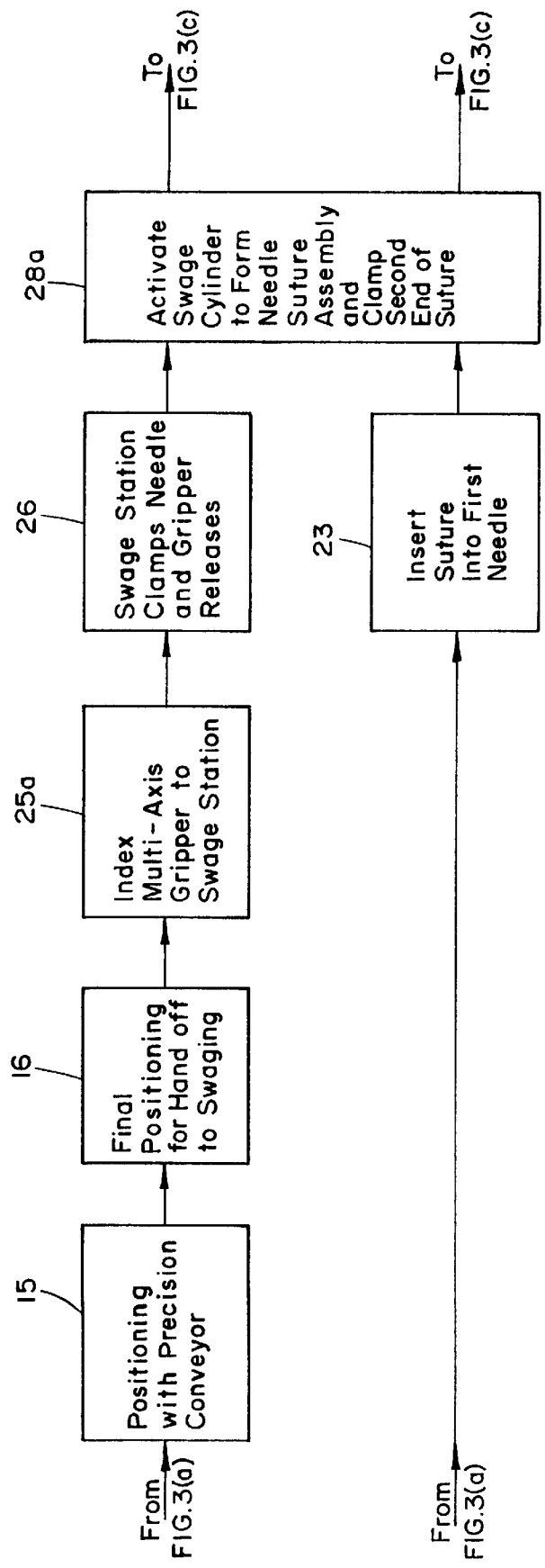
Figure 3C:
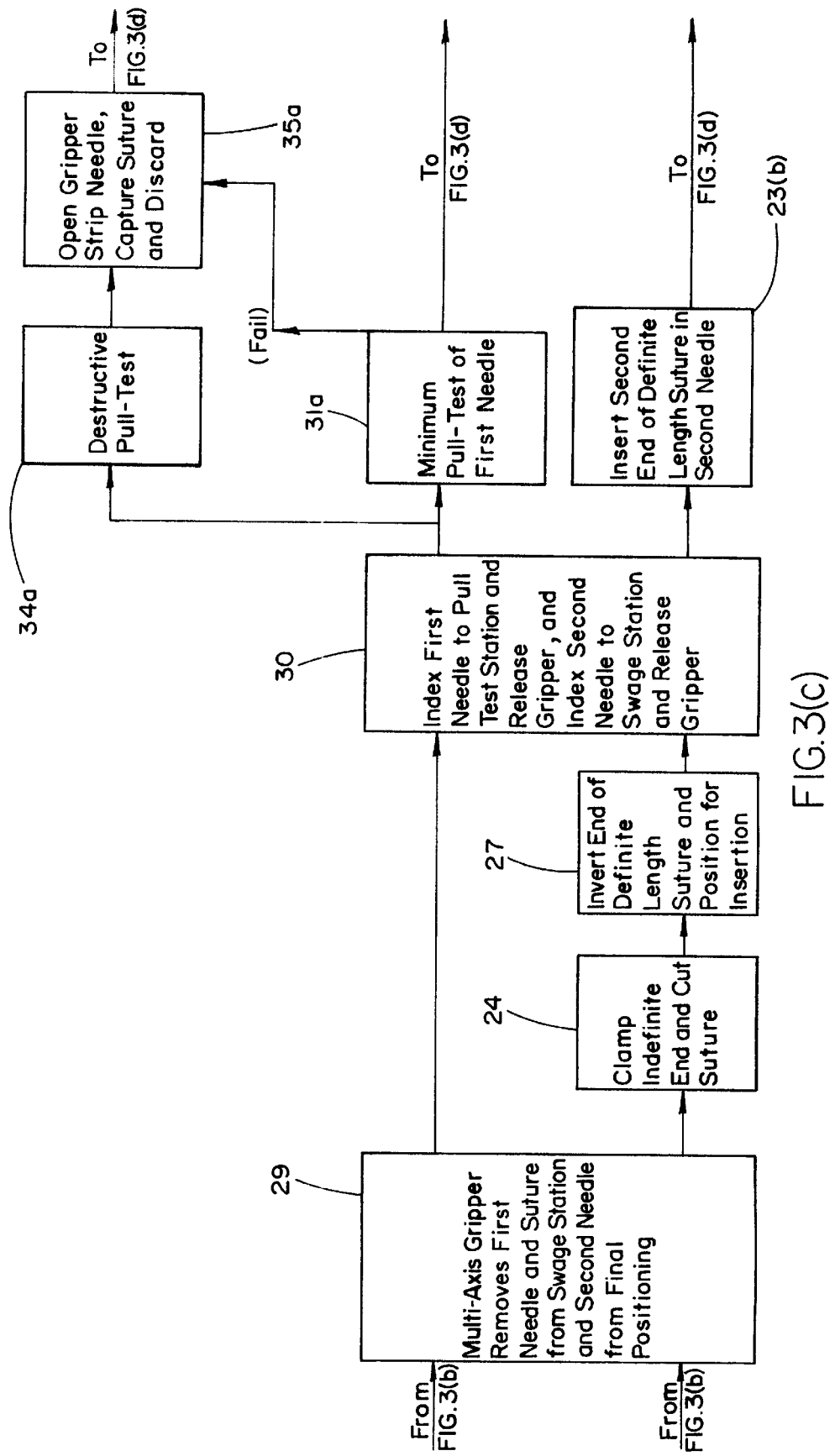
Figure 3D:
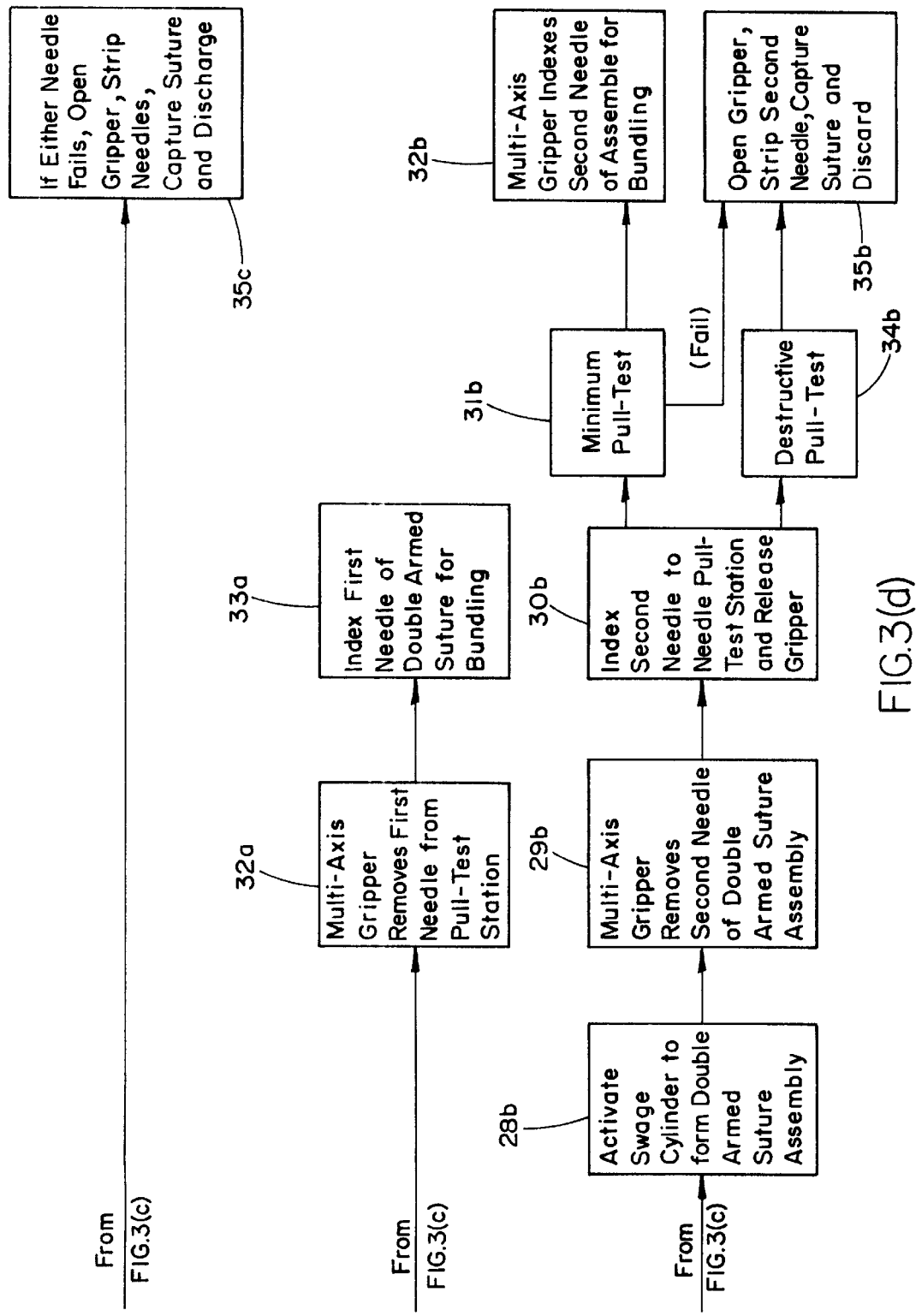

Simultaneous with the needle sorting process described above with respect to steps 10 through 25, an automatic suture cutting process takes place at the suture station 300 as shown in FIGS. 3(a) and 3(b) with respect to steps 18 through 28. Indefinite length suture material is supplied in various spools and configurations that may carry up to 5000 yards of material. This is indicated at step 18 in FIG. 3(a), where the suture material is loaded into a payoff assembly. A tension constant for the suture to be drawn is downloaded as indicated at step 19. A drawing tower apparatus includes grippers that alternately draw lengths of the suture material from the spool to enable cutting thereof which lengths are predetermined at step 20.

While the material is being drawn, it may require extra treatment or processing. For instance, as described in detail below, it may be desirable to heat the suture material under tension at the area which will become the suture tip in order to stiffen the material to facilitate the positioning thereof within the suture receiving opening of a surgical needle. Thus, at step 20, heat may be applied to a portion of suture material. In the preferred embodiment of the invention the heating step is performed upstream of the drawing and cutting apparatus to enable the suture to partially cool and harden before cutting. At step 21 of the block diagram of FIG. 3(a), the suture material is clamped and gripped by the servo grippers, and at step 22, the suture strand is drawn to a predetermined length and positioned for insertion within the suture receiving opening of the first needle of a pair for swaging.

Up to this point the formation of single armed sutures as described in U.S. Ser. No. 08/845,638 and the formation of double-armed sutures are the same, and the apparatus illustrated in the present invention can handle either process, as desired. If a single armed suture is desired, the indefinite end is claimed below the cutter, and the suture is cut as previously illustrated at step 24 in U.S. Ser. No. 08/845,638. When a double-armed suture is to be formed the invertible gripper is positioned to grip the suture at the second end above the cut axis. While the first end of the suture is inserted into the first needle. The needle is swaged to the first end of the suture at step 28, while simultaneously, the second end of the suture is clamped by the invertible gripper. The first suture clamp is unclamped and moved to a down position below the cutter, and the indefinite end is clamped as indicated at step 24 while the suture is cut between the two clamps. The suture is cut at step 24 to separate the suture of predetermined length from the indefinite length suture.

When a surgical needle is indexed to the swaging station 200 as described above, the universal gripper positions the needle in a precisely oriented position at the swage die opening formed at the ends of two swaging dies of a swage assembly as indicated as step 26 in FIG. 3(b). Simultaneously, the suture strand is drawn along a suture axis to register a tip thereof for insertion within the suture receiving end of the needle, as previously described with respect to step 22. Next, at step 23, the first gripper assembly at the drawing tower inserts the tip of the suture strand within a lower funnel guide for accurate positioning within the suture receiving opening of the needle that is aligned with the suture drawing axis. At step 28(a), the swage cylinder is activated to automatically swage the suture to the needle and the second end of the suture is clamped by the invertible gripper. The universal gripper is actuated to grip the needle, and then retracted on the rotary swage dial as shown as step 29. Before the rotary dial is indexed, the first gripper drops to the down position, and clamps the indefinite end of the suture as indicated at step 24, and the suture is cut. The first needle is then indexed to a pull-test station 400 at step 30 so that minimum pull-testing at step 31(a) or destructive pull-testing at step 34(a) may be performed. As the first needle is indexed, the second end of the suture is inverted, and the invertible gripper moves upwardly to the home or insert position as indicated at step 27 in FIG. 3(c).

As the first needle is indexed to pull testing at steps 31(a) or 34(a), the second needle of the pair is indexed to the swage station, and the universal gripper releases the second needle of the swage station as step 30 in the manner previously described for the first needle at step 26. The second end of the suture is inserted into the second needle at step 23(b) in FIG. 3(c), and the swage cylinder is again activated at step 28(b) to swage the second end of the suture to the second needle. Depending upon the results of the minimum pull-test, the needle and suture assembly will either be indexed by the rotary swage dial to the off-load station 500 where the armed needle will be bundled if the pull-test requirements are met (as shown as step 33(a) in FIG. 3(d)), or, will be discharged at the pull-test station if the needle fails the minimum pull-test (as shown as step 35(a) in FIG. 3(c)). The destructive pull-test always renders the needle incapable of further processing so the needle is automatically discharged at the pull-test station 400 as indicated at step 35(a) (b) in FIG. 3(c) (d). The second needle is similarly tested at steps 31(b) and 34(b) and passed on for bundling at step 32(b) or stripped and rejected as indicated at step 35(b) as previously described for steps 31(a) through 35(a). As indicated at step 35(c), if either of the needles fails the pull-test, both needles are stripped and the suture captured and discharged. Finally, as shown as step 33 in FIG. 3(b), needle and suture assemblies passing the minimum pull test are conveyed to an off-load station 500 where the individual armed sutures are bundled for subsequent packaging and sterilization.

A detailed explanation of the apparatus used to carry out each step in the suture cutting process will be explained in further detail hereinbelow.

Overview of the Aparatus

Figure 4:
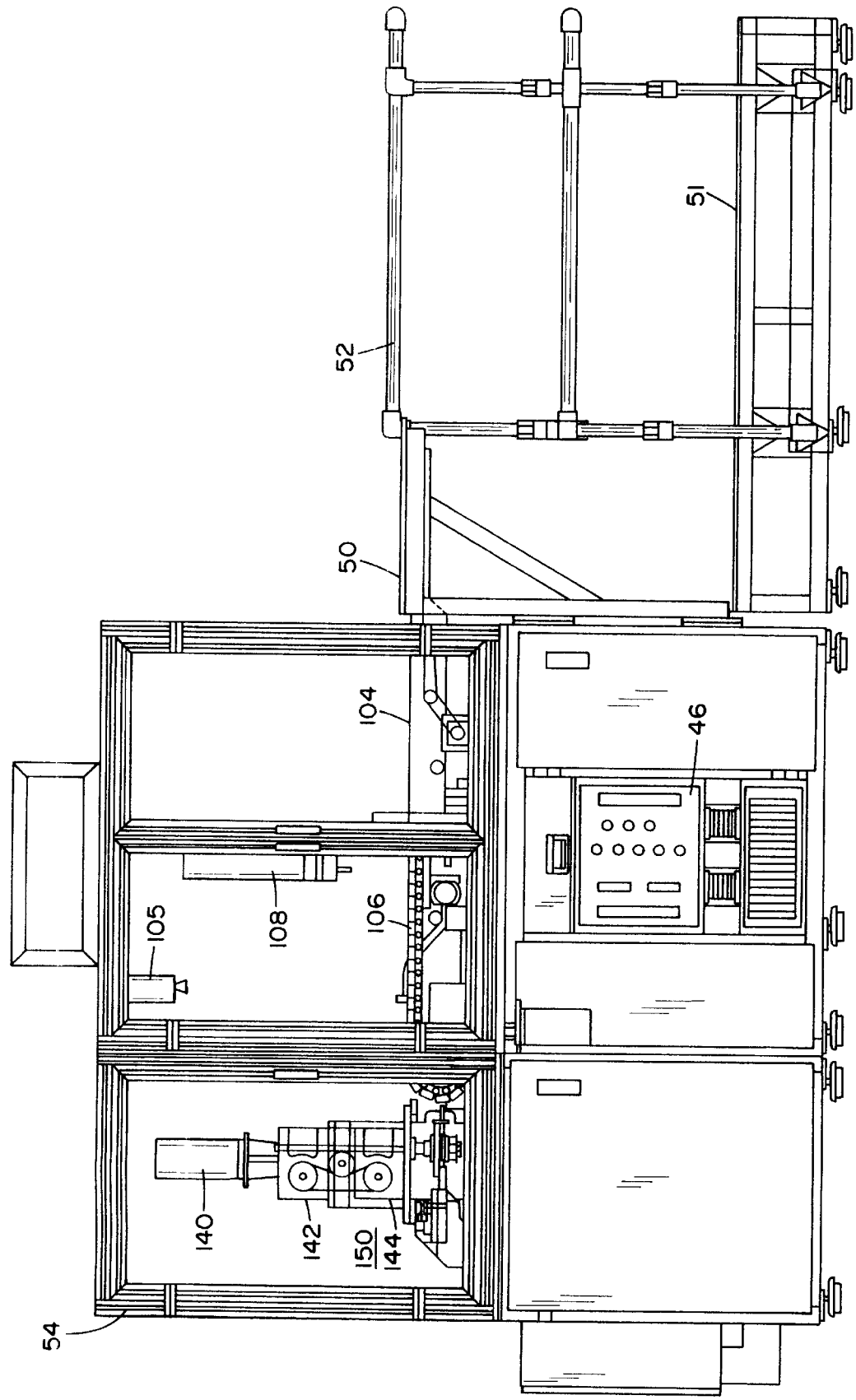
FIG. 4 is an elevation side view of the present invention illustrating an operator station, a control computer, portions of the robotic handling device, and the swage drive of the present invention.
Figure 5:
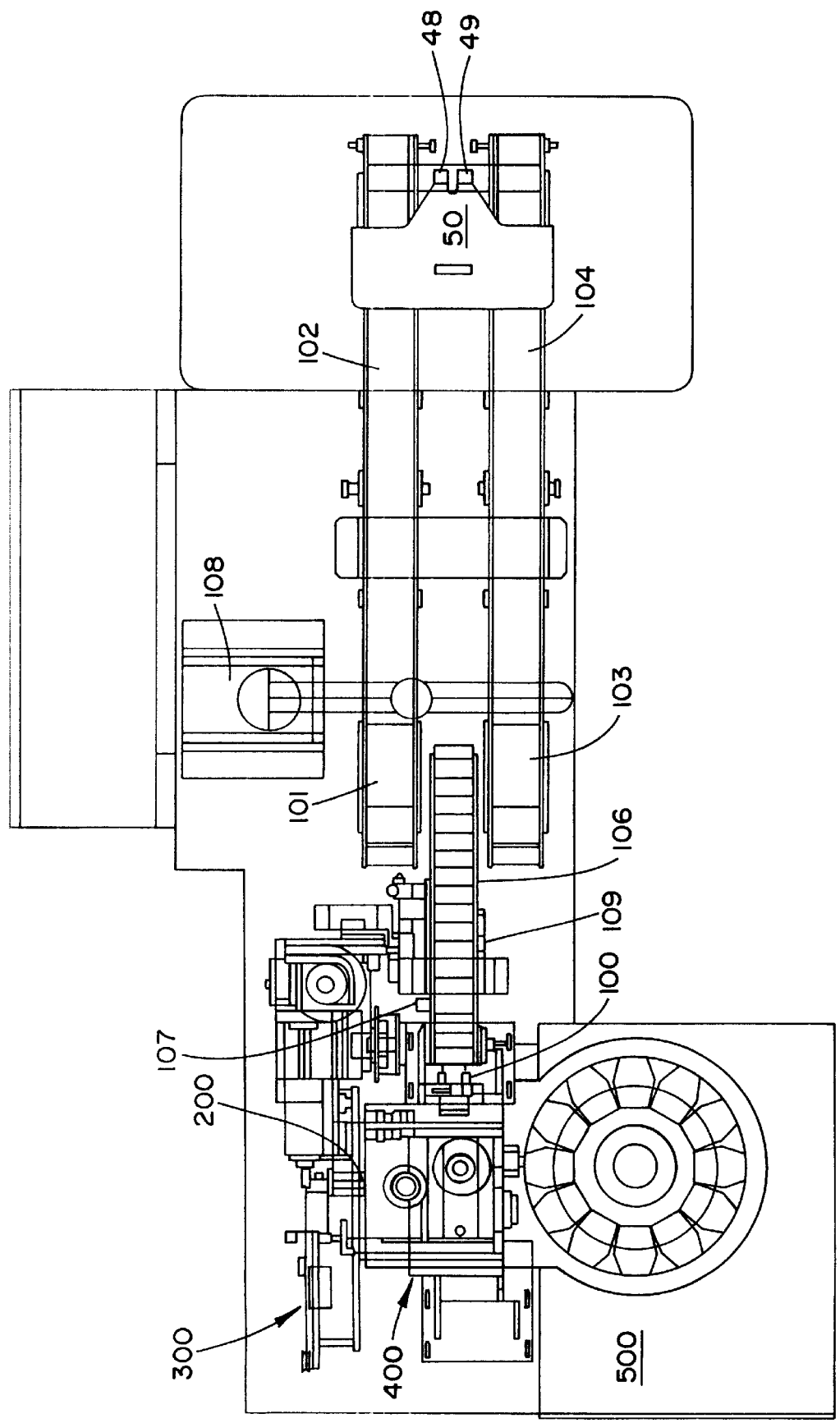
FIG. 5 is a top plan view of the present invention with the operator safety guards illustrated in FIG. 4 removed.
Figure 6:
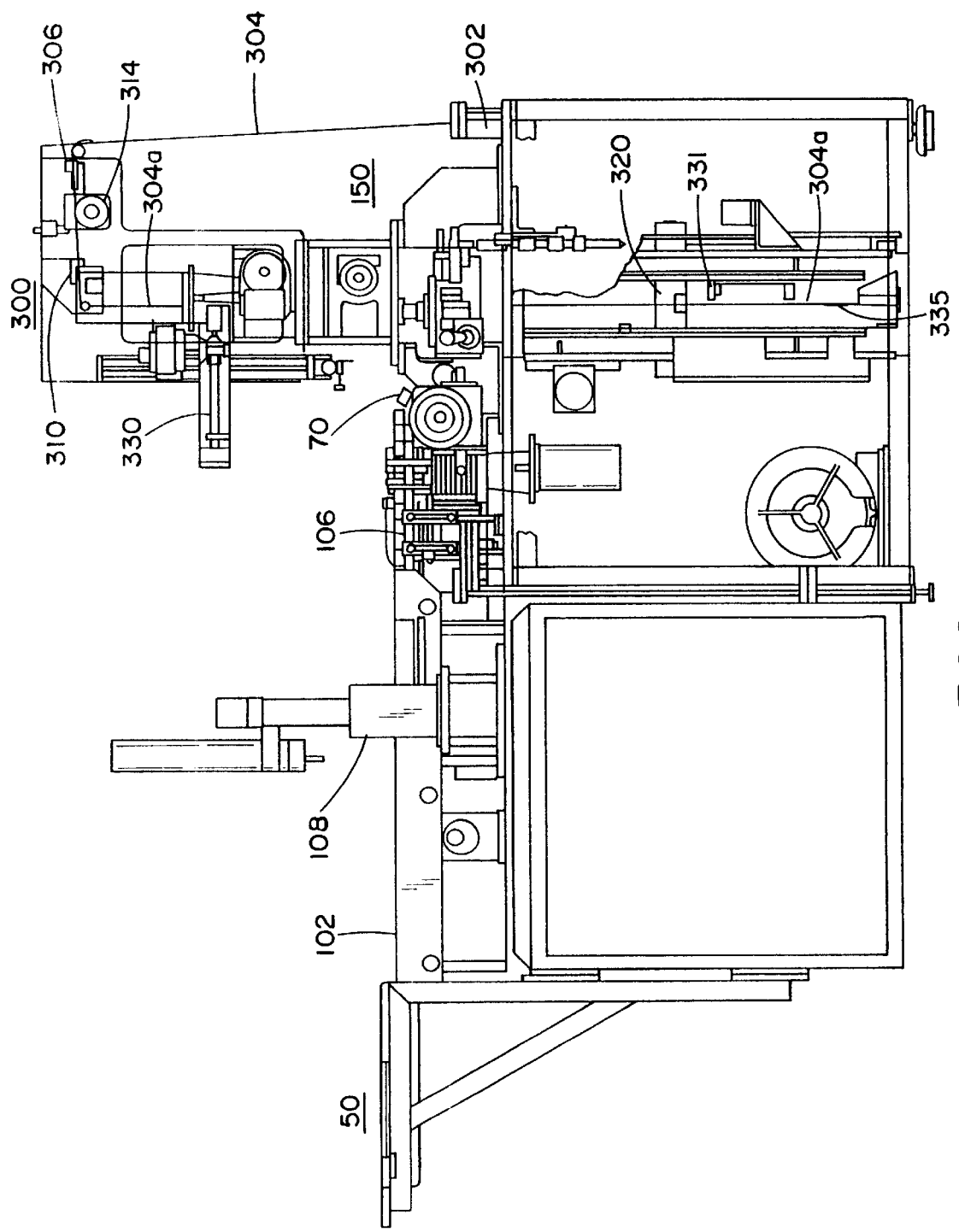
FIG. 6 is a detailed elevation side view of the present invention from the opposite side as illustrated in FIG. 4, with the operator safety guards removed.

FIG. 4 is an elevation view of one side of an apparatus constructed according to the teachings of the present invention, and FIG. 5 is a top plan view of the apparatus with the safety guards removed. FIG. 6 illustrates the apparatus from the opposite side as FIG. 4. FIGS. 4–6 are used in the following descriptive overview of the apparatus. This apparatus includes a singulation area or table 50 to assist an operator in singulating needles that are deposited to the translucent conveyors 102,104, one of the conveyors 104, being depicted in FIG. 4. The operator work station includes a platform 51 for operator seating and guard rails 52 for operator safety. Safety guards 54 are also provided around the machine for safety purposes.

Each of the needles singulated by the operator are dropped through openings 48,49 by sliding the needle along the table surface 50. This step avoids the needle to needle contact inherent in the vibratory feed bowls illustrated in U.S. Pat. No. 5,473,810 and thus substantially reduces the risk that premium needles or cutting edge needles will be blunted by needle contact. As each needle is dropped, it lands at an intermediate staging location, and at an appropriate interval, after each index of the indexing conveyor, the needles is blown by a puff of air to the translucent indexing conveyor, with needles dropped through opening 48 being transferred to translucent indexing conveyor 102 and needles being dropped through opening 49 being transferred to translucent indexing conveyor 104.

The needles thus transferred are indexed forward to imaging stations 101,103 wherein a back light provides a high contrast image of the needle against a white background for imaging purposes. The indexing conveyors 102, 104 are indexed approximately 2 inches at each index. By limiting the incremental advancement the image processing is step is enhanced, and problems associated with inertial loads on the needles on conveyors 102,104 are minimized. If the indexing conveyors 102,104 are accelerated too quickly, the needle will remain in its drop position and not be advanced forward, and conversely, if the needle is moving on the conveyor, and the conveyor is stopped too quickly, the needle will continue to travel after the conveyor is stopped. The present apparatus seeks to avoid either of these situations by minimizing the amount of index at each incremental step while still providing enough movement to provide an adequate supply of needles to the apparatus.

The needle singulating apparatus illustrated provides a single needle at each drop point which substantially enhances the accuracy of the vision system and minimizes needle returns that might otherwise be necessary for overlapping or nested needles that were either not imaged, or selected by the computer control means 39 for transfer by the robotic apparatus 108.

The needles deposited on the translucent indexing conveyor 104 are imaged by a vision system 105 and these images are processed by a computer control means 46 to identify the orientation and X,Y coordinate location of the needles. Determining the X,Y coordinates alone is not enough in the needle swaging environment inasmuch as the robotic apparatus needs to determine, in the case of a symmetrically formed curved needle, which end is the barrel end and which end is the cutting end in order to properly place the needle for subsequent automated handling. After both the orientation and location have been determined, a robotic apparatus 108 picks the needles from the translucent conveyors 102,104 and places them on a precision indexing conveyor 106. The precision conveyor 106 includes a plurality of "boats" 70 which are particularly adapted to provide precision positioning of the needle. The rotary swage dial 150 includes a drive motor 140 and first and second indexing transmissions 142,144 which are used to drive the swage dial in a manner as will be hereinafter explained in detail.

The needles transferred by the robotic apparatus 108 are transferred so that the butt end of the needle 44 is engaged by gripping jaws on the conveyor boats 70 of the precision conveyor 106. While the butt end is located and gripped by the robotic apparatus 108, at the point of pickup it may be oriented in either direction of curvature. For particularly small needles a fixed post may be provided for the robotic apparatus to use in correcting the orientation of curvature. For larger needles, a needle plow 109 is used so that the direction of curvature for each of the needles is uniform. As illustrated in FIG. 5, the apparatus also includes a prepositioner 107 which is adapted to approximately locate the butt end of the needle and an adjustable hard stop assembly at station 100 that precisely registers the butt end of the needle to an accuracy of 0.001 inches.

The needle singulation apparatus, and the operation of the indexing conveyors 102,104, the robotic apparatus 108 and the precision conveyor 106 is more fully described and claimed in U.S. Ser. No. 08/847,133, entitled "Semi-Automated Needle Feed Method and Apparatus," the disclosure of which is incorporated herein by reference thereto.

After the needle has been received at the precise positioning station 100, it is gripped by one of the universal grippers located on the swage dial mechanism 150 to be indexed through a plurality of stations including a swage station 200 wherein a suture of definite length is cut from a suture spool of indefinite length at station 300 and inserted into the needle at swage station 200 for permanent assembly thereto. After swaging, the needle is advanced to the pull-test station 400 for testing of the needle suture bond, and then indexed to a bundling station 500 wherein a plurality of buckets are circumferentially arranged on a rotating turntable to receive a predefined number of needles and sutures in each bundle.

Figure 17:
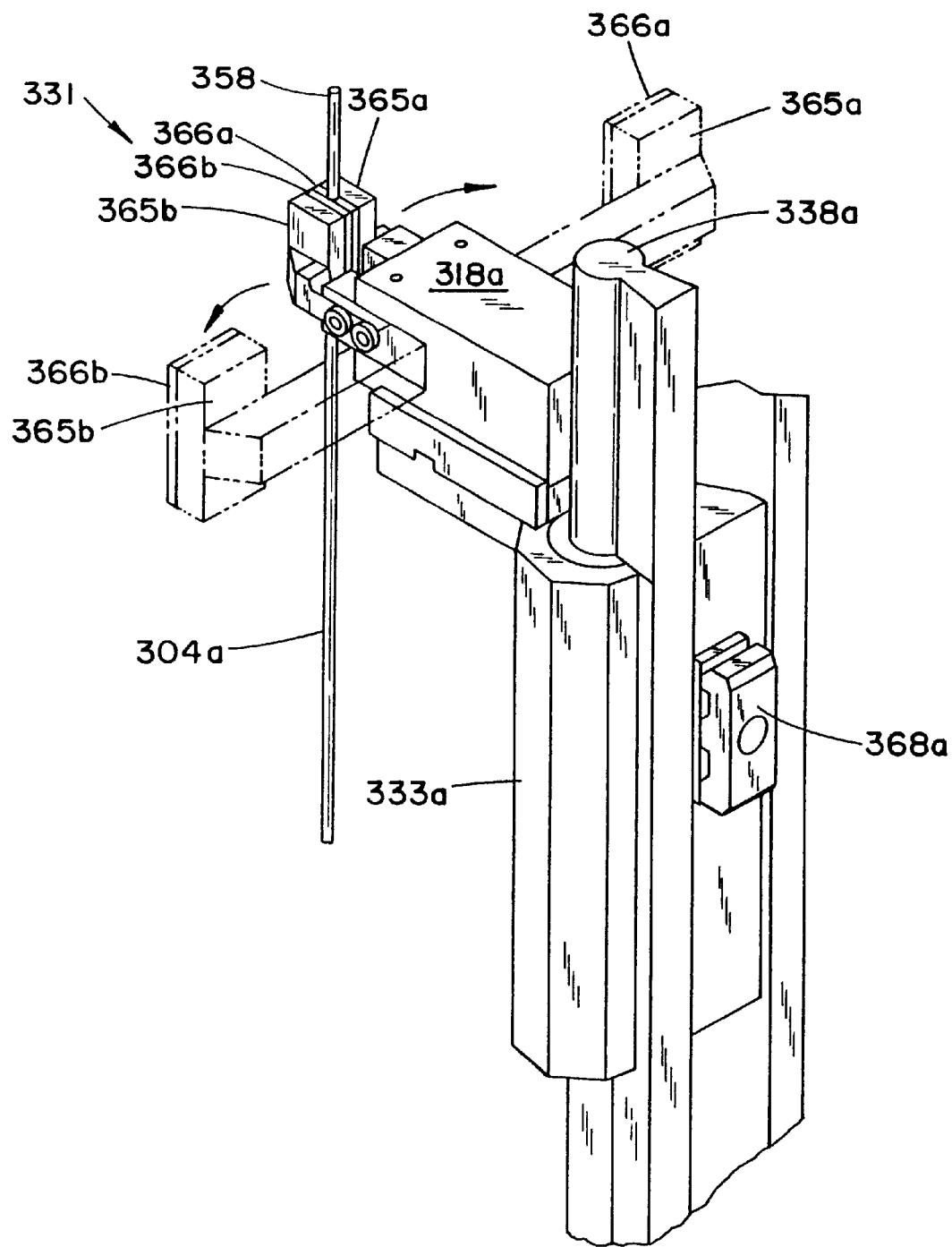
FIG. 17 is an enlarged isometric view of a suture gripper assembly having gripper arms shown in their open (dotted lines) and closed (suture gripping) positions.

FIG. 6 illustrates the apparatus of the present invention from the opposite side of the machine illustrated in FIG. 4 and includes breakaway portions to more particularly illustrate portions of the precision conveyor apparatus and the suture drawing and cutting station 300. As illustrated in FIG. 6, a spool of suture material 302 is mounted on a convenient location and the indefinite length suture material 304 is fed to the suture drawing station through a pretensioning apparatus 306, a tensioning roller 314 having a computer controlled tension constant which may be selectively downloaded from the computer control means 46 to match the suture material 304 being handled, and a knot detector 310 which may be used to provide a knot presence signal to the control computer 46 to reject that length of suture after swaging to a needle. From the knot detector 310 the suture strand 304a is fed through a tipping station 330 which heats the suture strand to a predetermined temperature to assist in tipping and cutting the suture for insertion into the surgical needle. From the heating and tipping station 330, the suture material is passed to the bottom of the machine to a turnaround roller 335 where it is grasped by the first and the second invertible suture clamps, one of which is illustrated at 331 which advance the suture material 304a in a hand over hand manner. As illustrated in FIG. 17, suture clamp 331 includes a traveling carriage 333(a) which reciprocates up and down vertical guide member 338(a) by means of a timing belt which is secured to the carriage at 368(a). A pneumatic actuator 318(a) includes first and second clamps 365a,365b and first and second gripping surfaces 366a,366b which clamp the suture material therebetween. The vertical guide member 338(a) is mounted within housing 337(a), illustrated in FIG. 9, with a corresponding vertical guide 338(b) and a corresponding housing 337(b) for the invertible gripper 332 on the opposite side of the drawing tower. The first and second suture clamps or grippers 331, 332 are reciprocated along the vertical guides 339(a), 338(b) by servo motors 336(a), 336(b) which are connected to the suture grippers 331,332 by the aforementioned timing belts (not shown) at 368(a), illustrated in FIG. 17, and 368(b) illustrated in FIG. 11(a).

Figure 19A:
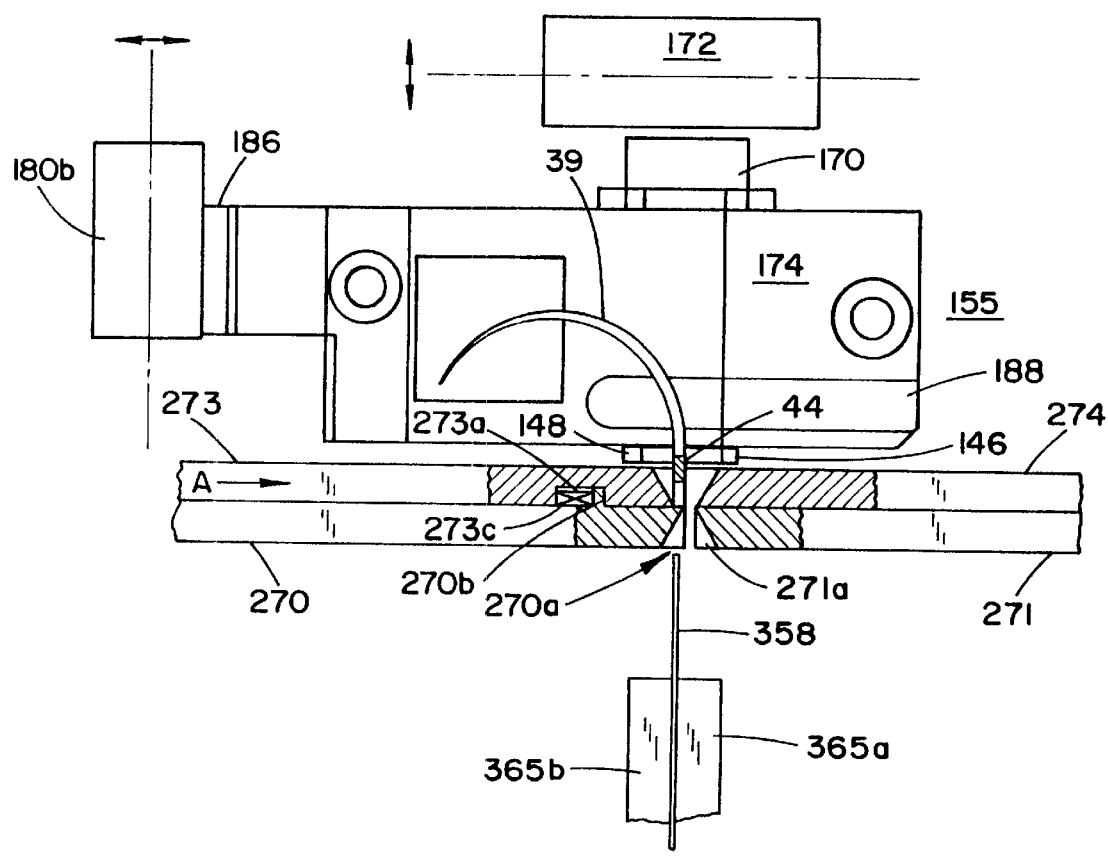
FIG. 19(a) is front face view of the universal gripper showing a surgical needle about to be placed in the swage dies of the present invention.
Figure 19B:
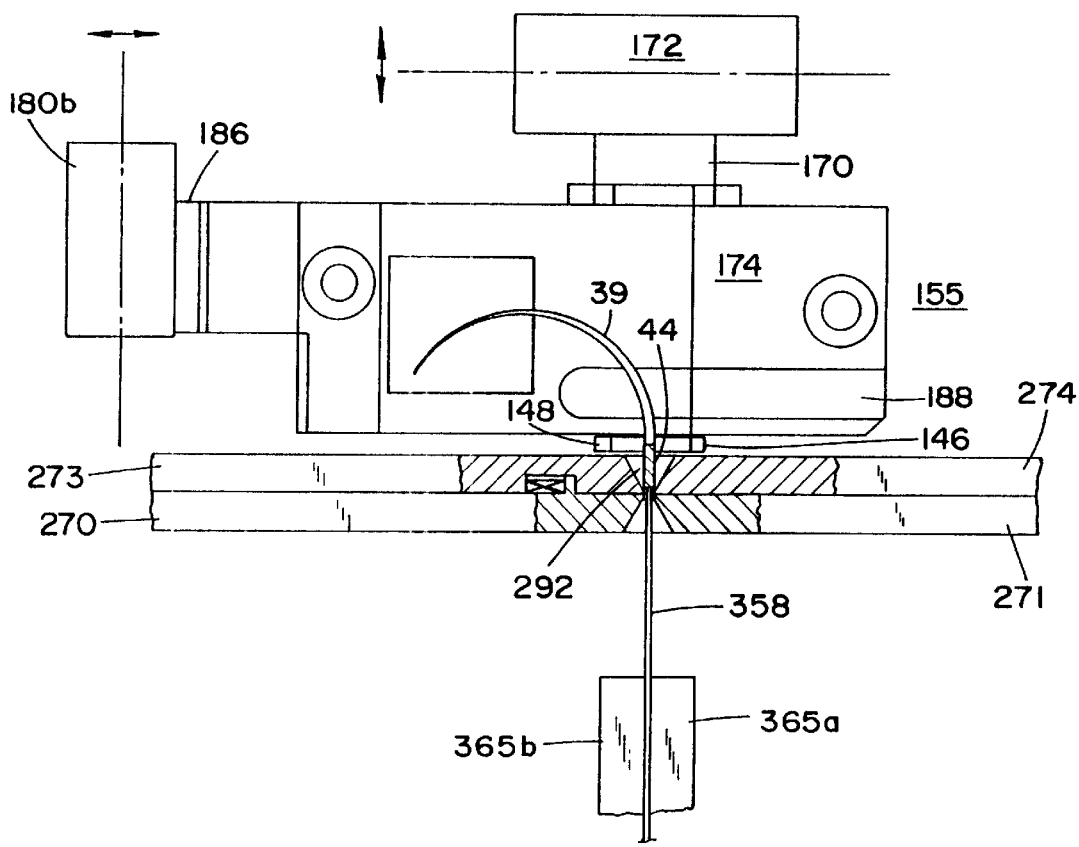
FIG. 19(b) is front face view of the universal gripper and a surgical needle with the universal gripper in a relaxed engagement, with the needle gripped by the swage dies of the present invention.

In a first cycle of operation, clamp 331 draws the suture of indefinite length to a suture insertion point immediately adjacent the swage plates of the swaging station and then dwells while the needle is positioned within the swage station 200. As illustrated in FIG. 19(b), the tip end of the suture 358 is positioned below a funnel dye formed in suture alignment plates 270,271 which reciprocate immediately below swage plates 273,374. After the suture tip end 358 has been inserted into the barrel end 44 of needle 39, the swage station is actuated driving the swage plate 273 against swage plate 274 to swage the suture tip 358 in the surgical needle 39.

Suture Drawing and Cutting

Figure 9:
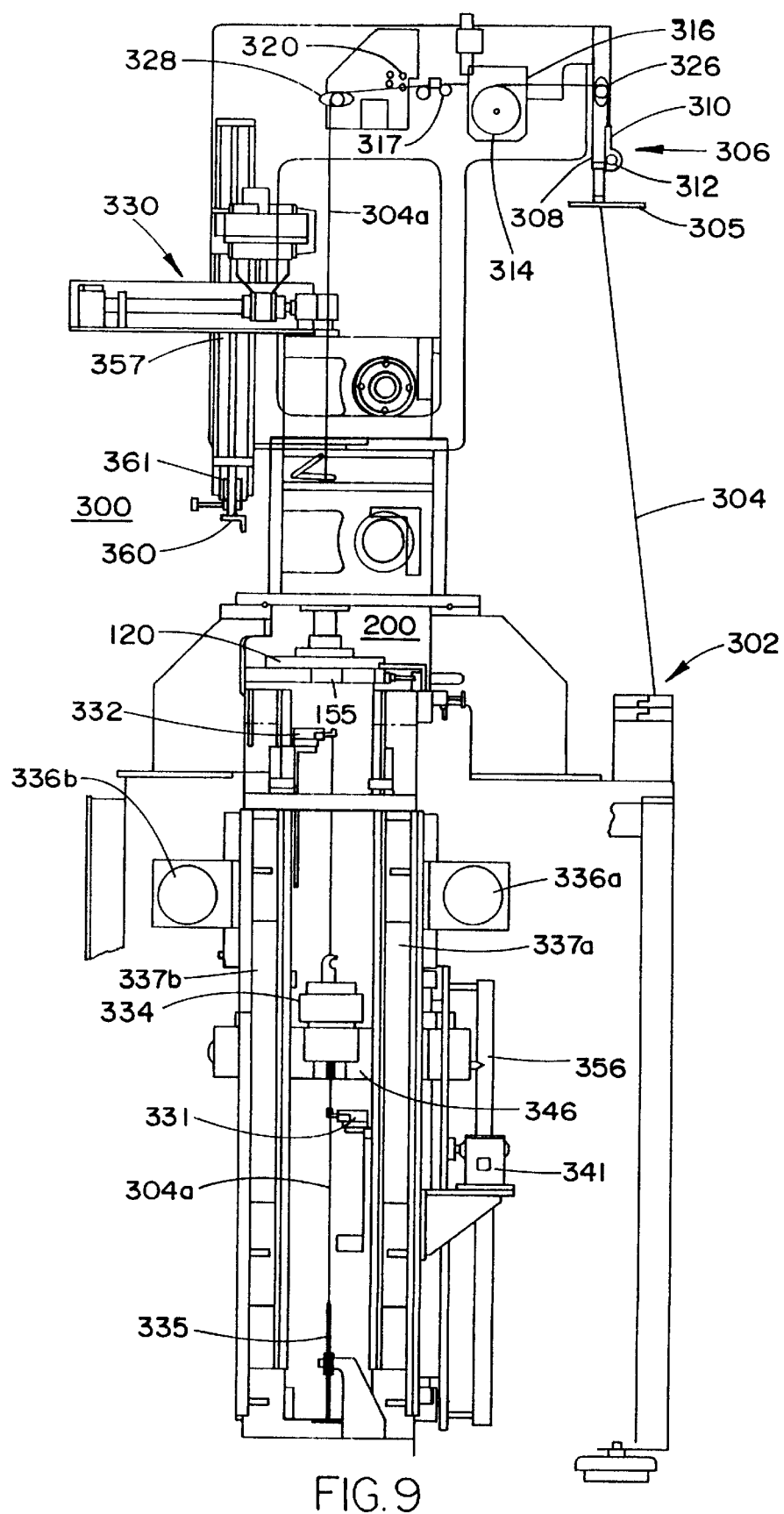
FIG. 9 is front elevation view of the suture drawing and cutting tower assembly used in the present invention.

FIG. 9 illustrates a front elevational view of one designed embodiment of a servo tower 300, similar to that shown in FIGS. 2–6, and shows the suture path therethrough. Suture 304 is pulled off one end of a supply roll 302 mounted to one side of the servo tower, through the center of an annular guide disc 305, and into a mechanical tensioner 306. The mechanical tensioner can comprise a stationary guide frame 308 and a pivotally mounted guide frame 310, pivotally mounted about a pin 312 at the lower end of the stationary guide frame. Each of the stationary guide frame and the pivotally mounted guide frame has a series of spaced guide elements, each with a central guide aperture therein, which are alternately interleaved, such that the spaced guide elements of the pivotally mounted guide frame alternate with the spaced guide elements of the stationary guide frame. The pivotally mounted guide frame 310 is spring biased about the mounting pin 312 to rotate the top thereof away from the top of the stationary guide frame, such that the suture extending between the alternating stationary guide frame elements and the pivoted guide frame elements is placed under tension while being pulled therethrough.

The suture then travels over idler roller 326, and extends to and is wrapped twice around a tension roller 314 which is mounted on one end of a torque motor 316, (illustrated in dotted lines in FIG. 9) which applies a given tension to the suture as it is pulled through the servo tower by the first and second gripper assemblies 331, 332 when a single needle suture assembly is prepared, the gripping assemblies alternate in a hand over hand advancement as previously described in U.S. Ser. No. 08/181,595, entitled "Suture Cutting System," the disclosure of which is incorporated herein by reference thereto. When a double-armed suture is prepared according to the present invention, a different gripper assembly and a different methodology is employed.

Each different suture size and material has a different tension applied thereto as it is drawn through the apparatus. The torque motor 316 provides a different tension force for each different suture size and type, and the specific tension force(in grams per volt to be applied by the torque motor) is downloaded from a computer program at each suture batch changeover. The proper tension is important for several operations described herein, and is particularly important for the cutter assembly to operate while providing a clean neat cut without a broom effect.

The suture then extends to an out-of-suture sensor positioned at 317, and then through a knot detector 320. The suture 304 then travels to a second idler roller 328 to change direction again, from which the suture 304 extends vertically downwardly through a heated tipping assembly 330, which heats and ultimately stiffens a small length of the suture, at which small length the suture is subsequently cut and the cut tip 358 is inserted into and swaged to a needle.

The suture 304 then extends downwardly from the tipping assembly to a large idler roller 335 mounted near the bottom of the machine having an appropriately 7 inch diameter, at which the suture reverses direction and travels vertically upwardly to the first and second gripper assemblies 331, 332, to the suture cutter assembly 334 and a suture swaging assembly 200. As illustrated in FIGS. 19(a), (b), during the insertion operation, the cut suture end is guided by a funnel shaped aperture 270(a), 271(a) in a suture guides 270,271 into the aperture in the end of a needle, after which a moving anvil 273 is moved relative to a stationary anvil 274, of a swage die, to swage and attach the needle to the suture.

In this embodiment, after initialization, one gripper assembly will be in a home position, 2" below the face of the swage die mounting surface, allowing a 2.03" movement from the home position to an insert position. A proximity switch is located on each tower at 2" below the face of the swage die mounting surface to set the home position during an initialization procedure.

Assuming that the machine is being initially set up to cut a desired length of suture, the cutter assembly 334 will be moved to a predetermined vertical position in the swaging machine by operation of the handcrank attached to gearbox 341. This is done by aligning a pointer for the cutter assembly with a vertical scale 356 positioned on the side of the swaging machine, similar to the vertical scale 357 shown above for the tipping assembly.

The cutter assembly includes a proximity switch thereon, and during an initialization procedure, the position of a gripper assembly is detected by the proximity switch, and that position is set in memory to set the servo gripper bottom position for gripper 332 during subsequent normal operation of the machine. The tipping assembly is also moved to an appropriate position in the machine as described hereinbelow.

The present invention is capable of two modes of operation. In the original mode, it forms a single armed suture, as described in the parent application, while in the second mode, it forms a double-armed suture. The two modes of operation vary significantly in their suture handling methodology, so each mode is described separately.

Single Armed Suture Mode

FIG. 9 illustrates the right gripper 331 positioned slightly below the cutter assembly 334 so that the indefinite length strand will be gripped when the definite length swaged strand is cut. Thus, the upper left gripper 332 now grips the suture material 304 having a tipped end 358 and it now becomes the lead gripper. The next cycle begins with the lower right gripper 331 vertically drawing the material 304 along the height of the drawing tower 300 for the long stroke to position the next strand to be cut for insertion within the surgical needle.

During this operation, assume that the upper left gripper assembly 332 has just moved to its down position. At the same time, the gripper assembly 331 stops at the upper home position, and waits a predetermined time, during which a needle is preclamped in an insertion position in the swaging station 200. The gripper assembly 331 then moves to the insert position to insert the suture tip in the suture receiving opening formed in the barrel of needle 39.

The following operations are then performed substantially simultaneously. The bottom gripper assembly 332 closes, a tipping operation is performed simultaneously upstream at the tipping assembly 330, and the swage station is simultaneously actuated to swage the needle end around the suture, attaching it thereto. Thereafter, the cutting assembly 334 is activated, cutting in the previously tipped and now hardened area to cut the suture to the given length. Thereafter, the upper gripper assembly 331 opens, and the assembly 331 returns to the bottom position, and simultaneously therewith the lower gripper assembly 332 moves up to the home position, and the cycle is then repeated.

Double-Armed Suture Mode

To form double-armed sutures, that is a suture having a surgical needle attached to either end thereof, requires that one of the gripper assemblies 331,332 be altered to provide an invertible or rotatable gripper, such as the invertible gripper illustrated in FIGS. 11 and 12(a), 12(b). In addition, the gripping and cutting methodology is significantly altered. The invertible gripper will be described with reference to FIGS. 11–12(b) while the gripping and cutting methodology will be described with respect to FIG. 10.

As illustrated in FIGS. 11–12(b), the invertible suture gripper 332 reciprocates along a pair of vertical guide members 338(b) and 338(b)' mounted in housing member 337(b). They are reciprocated by a servo motor 336(b) (illustrated in FIG. 9) which drives a timing belt attached to clamp member 336(b). The clamping jaws 365(a)', 365(b)' and the suture gripping surfaces 366(a)' and 366(b)' are identical to the suture gripping arms used in the suture gripper 331 previously described with respect to the illustration of FIG. 17. Likewise, pneumatic cylinder 318(b) actuates the gripping arms from an open to closed position as illustrated in FIG. 11 in the same way as that previously described with respect to FIG. 17.

As illustrated in FIG. 12(a) the pneumatic actuator 318(b) is mounted on an invertible or rotatable L-shaped frame member 339 which rotates about axis A–A' on shaft member 340 which is journalled for rotation within the carriage member 333(b). On the lower portion of carriage 333(b) is another stepper motor 342 which provides for rotation or inversion of the suture gripper 332, and specifically, the gripping jaws 365(a)', 365(b)' and their respecting gripping surfaces. As illustrated, the suture gripper 332 is inverted in FIG. 12(a), and rotated to the insertion position in FIG. 12(b) (illustrated in dotted lines). Rotation or inversion of the gripper jaws is accomplished by stepper motor 342, driving sprocket 343, drive chain 344 and driven sprocket 345 which is keyed to shaft member 340. In other respects, the gripper assembly 332 is actuated in much the same manner as gripping member 331 wherein the gripping jaws 365 are opened by one gripper to permit passage of the other gripper in the closed position when the grippers pass each other on their reciprocal path along the drawing axis of the suture tower. If gripper member 331 has gripped the suture and is traveling upwards as illustrated in FIG. 9, then jaws 365(a), 365(b) will be closed and gripping the suture as illustrated in FIG. 17. While this gripper is reciprocated upwardly, the invertible gripper 332 is reciprocated downwardly with the jaws in the open position as illustrated in FIG. 11. Conversely, when suture gripper 332 has gripped the suture and is traveling upwards, the gripping jaws 365(a)', 365(b)' are in the closed position while the gripping jaws 365(a), 365(b) are in the open position illustrated in dotted lines in FIG. 17.

Figure 10:
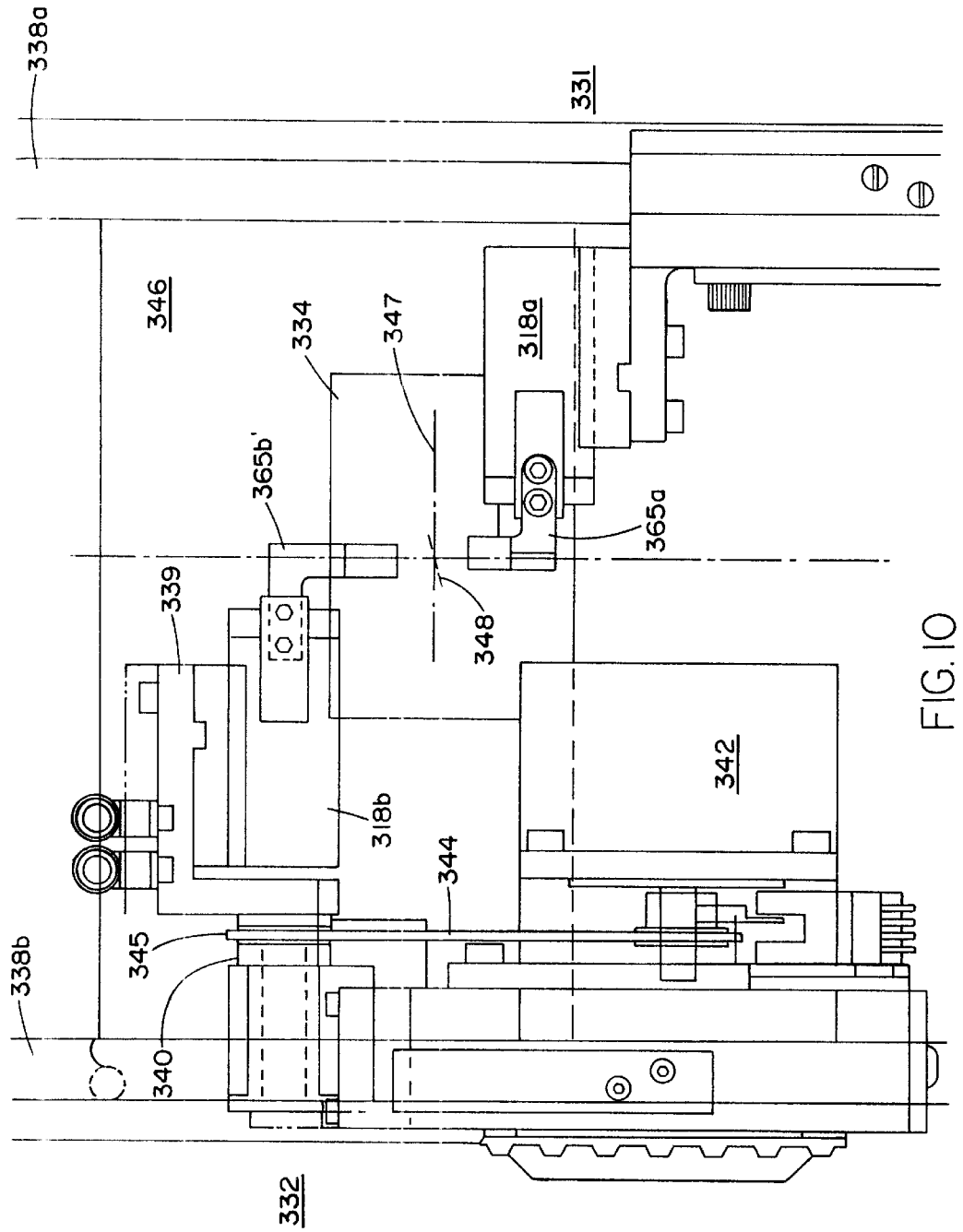
FIG. 10 is an enlarged front elevation view of the suture drawing assemblies used in the present invention, and their relationship to the cutting axis at the time the cut is made.

The suture cutting and insertion methodology between single armed needles and double-armed needles is substantially different inasmuch as the swaging of single armed sutures requires twice as many cuts to the indefinite length of suture strand as does the swaging of double-armed sutures. The suture handling methodology will be described with respect to FIGS. 9 and 10. As illustrated in FIG. 9, suture gripper 331 is in the down position and suture gripper 332 is in the home position, immediately prior to the insertion position. This is typical of single armed suture positioning. However, in double-armed positioning, the typical tower sequence begins with suture gripper 331 down with the gripper closed on the indefinite length of suture while the second suture gripper 332 is also down, with the gripper arms open and inverted as previously described with respect to FIGS. 12(a) and 12(b). Suture gripper 331 then reciprocates upwardly to its home position as the universal gripper indexes the first needle of the pair into position for insertion into the swage station 200. During this insertion, the universal gripper extends, as will be hereinafter described with respect to FIGS. 14–19 to place the needle between the swage dies of the swage station as illustrated in FIG. 19(a). The swage dies then preclamp the needle in position as illustrated in FIG. 19(b) while the universal gripper releases the needle. The first suture gripper 331 then moves to the insert position to insert the suture into the needle as illustrated in FIG. 19(b) and the needle is swaged by the swage dies as will be hereinafter later described with respect to the swage station. After swaging, the needle is regripped by the universal gripper as the swage jaws are retracted. Simultaneously, the second suture gripper 332 grips the suture above the cutting axis as illustrated in FIG. 10 with the jaws inverted. The first suture gripper 331 is then opened and reciprocated downwardly to its down position below the cutting axis as illustrated in FIG. 10 and the clamping jaws are closed on the suture.

FIG. 10 illustrates the relative positioning of the first suture gripper 331 and a second suture gripper 332 immediately prior to the suture cut. As illustrated, the parts have been enlarged somewhat for purposes of clarity of illustration and it should be noted that in the normal operating sequence, the two suture grippers will grip the suture approximately 0.350 inches apart.

As will be hereinafter described, the cutter mechanism 334 is mounted on a moveable support frame 346 which is reciprocated upwardly and downwardly by drive motor 341 to provide a desired suture cut length as the suture is severed from the indefinite length strand of suture 304(a). Likewise, the down positions of suture grippers 331,332 are altered by the computer controlled servo motors 336(a), 336(b) to accommodate the desired suture cut length. The cutting mechanism 334 cuts the suture along an axis illustrated at 347 in FIG. 10. The cutter traverses a diagonal axis illustrated at 348, to create a diagonal cut which occurs in the heated or pretreated zone to form a pair of suture tips on either side of the cut axis 347.

Immediately after the cut, the suture gripper 332 is reciprocated upwardly to its home or insert position as illustrated in FIG. 9. Simultaneously the gripper and the second end of the suture are rotated by drive motor 342, drive chain 344 and driven sprocket 345 about the axis of shaft 340 to the insert position illustrated in dotted lines in FIG. 12(b). Simultaneously, a second universal gripper is indexed or rotated to position the second needle of the pair of needles in the swage station for swaging. The second universal gripper is then extended to place the needle within the jaws of the swage mechanism and the needle is preclamped for precise positioning. After the universal gripper has released the needle, the invertible suture gripper 331 moves to insert the suture into the needle as previously described with respect to FIG. 19(b) and the second needle is then swaged.

Simultaneously with this operation, the first needle of the double-armed pair is undergoing pull-testing at the pull-test station 400. After the second needle has been swaged in the swage station, the universal gripper regrips the needle and the suture gripper 332 releases its grip on the suture. Immediately thereafter, the swage station releases the needle and the universal gripper reciprocates radially inward to remove the needle from the swage station.

As the suture gripper 332 releases the suture, its jaws are opened to the open position, and it is reciprocated downwardly to the position illustrated in FIG. 10. While it is reciprocated downwardly, the suture grippers 365(a') and 365(b') are inverted on the rotatable carriage 339 so that when suture gripper 332 arrives at its down position the jaws are open and inverted. The first suture gripper 331 is then reciprocated upwardly between the open jaws of suture gripper 332 to the home position, and as it reciprocates upwardly, it draws a new length of suture from the strand of indefinite length as a new needle is being loaded into the swage station, thus completing one cycle of operation of the device. As the new needle of the second pair of armed sutures is rotated into place, the second needle of the double-armed suture is positioned for pull-testing while the first needle is stripped for collection at the collection and bundling station 500. The suture insertion and swaging steps are completed on the first needle of the second pair and as that needle is indexed to the pull-test station, the second needle of the first pair is likewise ejected and collected at the suture collecting and bundling station 500.

After removal of the swaged needle and attached suture length from the apparatus, it is subjected to a sterilization operation, during which the suture length incurs some shrinkage. Accordingly, the cut lengths of suture must be cut to lengths slightly longer than their desired(or label) final lengths to compensate for such shrinkage.

As described above, after heating of a predetermined length of suture at the tipping assembly, the suture must cool to allow setting and hardening of the suture material prior to cutting of the suture at the hardened length and insertion of the cut stiffened end into a needle. This cooling of the suture is provided in this embodiment by allowing a discrete number of machine cutting cycles to occur between tipping of the suture and cutting of the suture. This is provided by allowing a predetermined long length of suture travel between the tipping assembly and the cutter assembly. Hence, the suture tipping assembly 330 is positioned near the top of the servo tower, and after heating thereat, the suture travels to the bottom of the machine, around the large idler roller 335, and then back upwardly to the cutter assembly 334. The large diameter of the idler roller 335, relative to the other idler rollers 326, 328, is provided because the small length of suture which has been heated at the tipping assembly 330, has begun to harden and set by the time the heated section reaches the large idler roller. The large diameter thereof facilitates the suture to travel therearound without picking up a permanent curved set from the large idler roller, as it is desirable for the suture to be straight, without any curve, when it is subsequently cut and inserted into a needle. The idler rollers 326 and 328 typically have a 0.5 inch diameter, whereas the large diameter roller 335 has a diameter preferably greater than 6.0 inches, approximately 7.0 inches in one embodiment.

The operation of the machine depends upon a discrete whole number of machine cutting operations to be performed between the tipping and cutting operations. Accordingly, for each different length of cut suture, the tipping assembly 330 must be positioned at a different predetermined position within the machine for the tipped section of suture to be precisely and correctly positioned at the cutter assembly 334 after a given number of machine cycles.

The following table gives in its columns, proceeding from left to right, the label suture length, the actual cut suture length, the number of machine cycles or increments provided between tipping and cutting, the total travel length of the suture between tipping and cutting, the tipping assembly vertical position above the table top, and the tipping assembly scale pointer position above the table top (explained in greater detail hereinbelow).

| SUTURE LENGTH | | | | ABOVE TABLE TOP | |
| --- | --- | --- | --- | --- | --- |
| LABEL | ACTUAL | INCREMENTS | TOTAL | TIPPER C | POINTER |
| 18 IN. | 19 IN. | 6 | 114 IN. | 27.64 IN. | 25.89 IN. |
| 27 IN. | 28 IN. | 4 | 112 IN. | 25.64 IN. | 23.89 IN. |
| 30 IN. | 31 IN. | 4 | 124 IN. | 37.64 IN. | 35.89 IN. |
| 36 IN. | 36.25 IN. | 3 | 108.75 IN. | 22.39 IN. | 20.64 IN. |

Figure 13A:
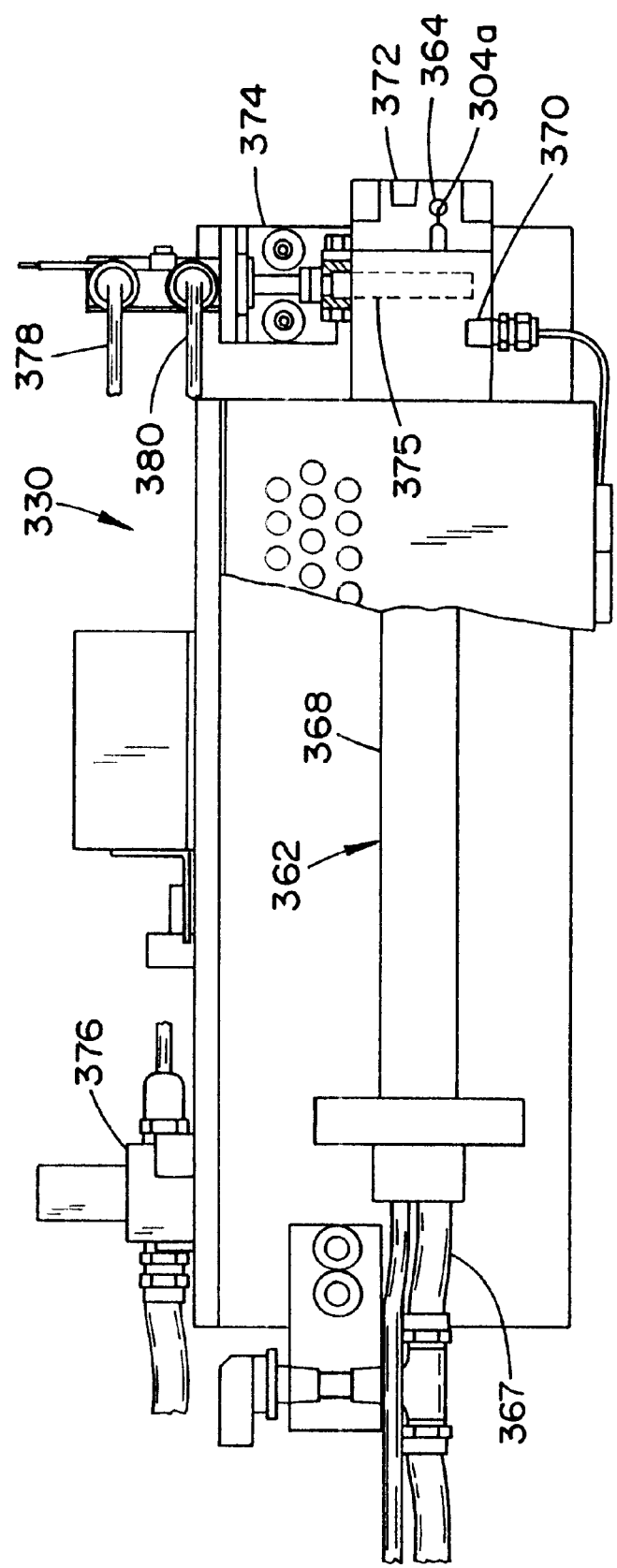
FIG. 13(a) is top plan view of the suture tipping assembly used in the suture drawing and cutting apparatus of the present invention illustrated in FIG. 9.
Figure 13B:
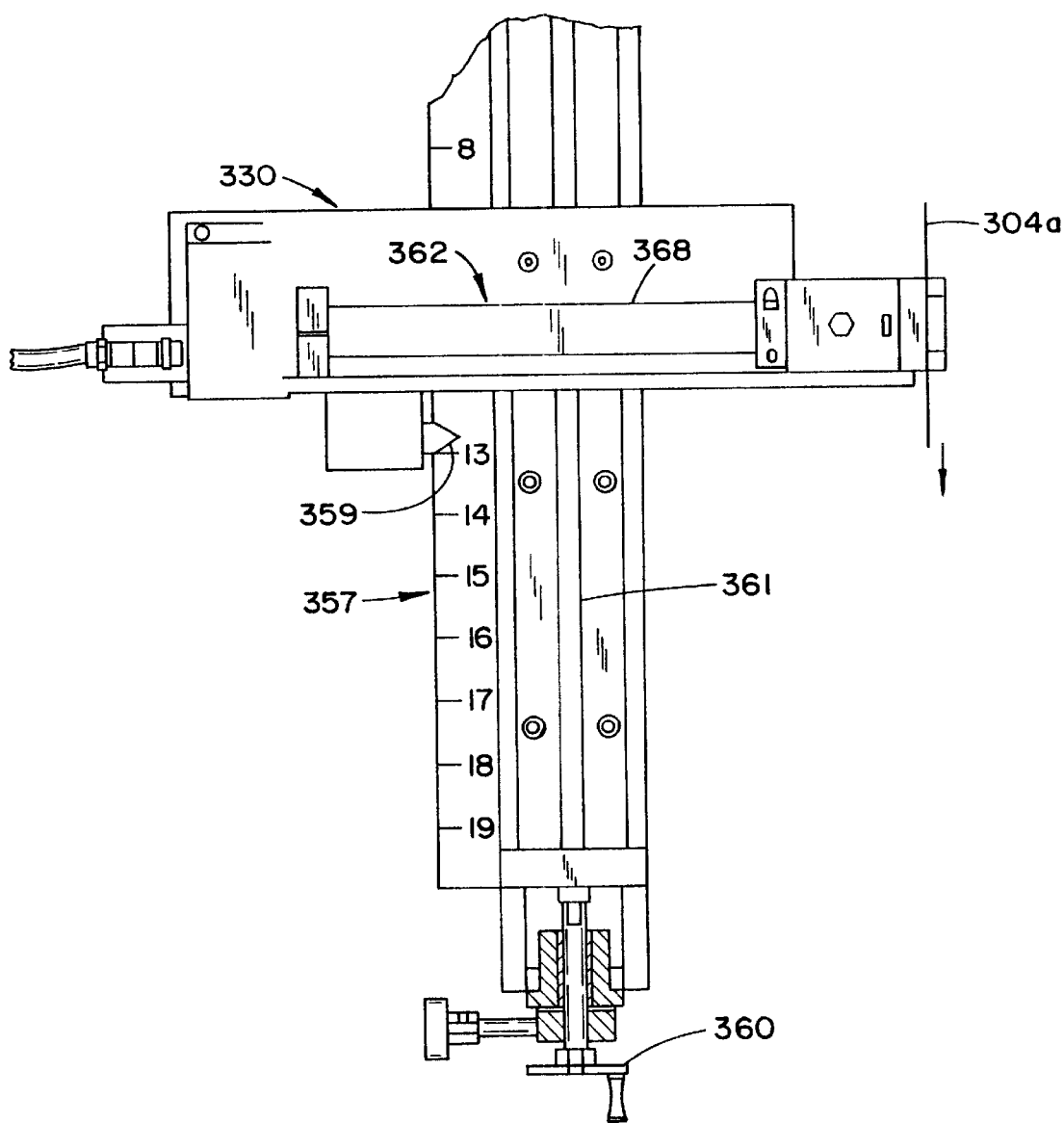
FIG. 13(b) is front elevation view of the suture tipping assembly illustrated in FIG. 13(a) and used in the suture drawing and cutting apparatus of the present invention.

FIG. 13(b) illustrates an enlarged front elevational view of the suture tipping assembly at which a small length of the suture is heated to stiffen the suture material after subsequent cooling thereof, in preparation for cutting a given length of the suture and inserting the lead cut end of the suture into the end of a needle for swaging thereto. FIG. 13(b) illustrates the movement of the tipping assembly 330 along a vertical scale 357 provided adjacent to the tipping assembly 330. The vertical position of the tipping assembly in the machine is adjustable by a handcrank 360 and precision lead screw 361, similar to the positioning mechanism for the cutter assembly as described hereinabove. As the handcrank is rotated, the vertical position of the tipping assembly 330 in the machine is changed, and is precisely positioned by reading a pointer 359 attached to the tipping assembly on the scale 357. A chart is provided for the machine which gives, for each desired length of suture, the appropriate position for pointer 359 of the tipper assembly 330 on the vertical scale 357, and a similar position for the cutter mechanism 334 on the vertical scale 356.

In this embodiment, the position of the cutting mechanism along the drawing axis is continuously adjustable to provide an infinite number of possible different lengths of cut suture. For each different cutting position of the cutting mechanism, the tipping mechanism is adjustably positioned at a different predetermined position in the apparatus to provide for the tipped section of suture to be precisely positioned at the cutter mechanism for a discrete number of machine cycles.

In an alternative embodiment which does not have this infinite adjustment feature, several standard lengths of suture are accommodated by several standard positions which are fixed in the machine by pins which secure the cutter mechanism to the machine frame by pin receiving holes in the machine at the standard positions. For example, the cutter mechanism might be moved to a position for cutting 18" sutures and be secured to the frame by the placement pins being inserted into the pin receiving holes in the machine for 18" sutures. The cutter mechanism might also be moved to positions for cutting 27", 30", or 36" sutures by moving the placement pins to the pin receiving holes in the machine provided for those length sutures. Each different position can have a separate proximity switch provided therefor, which indicates the cutting mechanism position to the controller, which then downloads the appropriate servo gripper bottom position. The appropriate tipping mechanism position is known for each different cutter mechanism position.

FIGS. 13(a) and 13(b) illustrate a heater 362 in the tipping assembly 330 and the vertical movement of the suture 304(a) down (front view, FIG. 13(b)) and through (top view, FIG. 13(a)) a suture tipping aperture 364, FIG. 13(a), positioned on the right side of the tipping assembly. FIG. 13(a) illustrates further details of the flow of heated air through the tipping assembly and its control to selectively heat and tip the suture. As described previously, the tipping assembly 330 is mounted near the top of the machine so that it takes a discrete number of machine cycles for the suture to reach the cut position. This gives the tipped area time to cool down before the cutting and insertion operations. The tipping assembly operates by flowing air supplied at a regulated pressure through an inlet air duct 367 at a regulated flow rate, in one embodiment 195 CFH (Cubic Feet per Hour), over a heater coil mounted within an outer heater casing 368. Air is supplied to a flowmeter at a regulated pressure required to maintain 195 CFH of air flowing over the heater coil. A thermocouple 370 is positioned in the air flow at the discharge end of the heater casing 368, to monitor and control the air temperature through a controller in a programmable logic controller (PLC). The tipping assembly 330 is operated at various temperatures between 200° F. and 550° F. depending upon the particular suture material to be run. The particular temperature is a down loaded parameter from an operating program at each suture batch changeover. The tipping assembly guides the suture and provides a 2.000" long heating aperture 364 for the tipping length.

The constant flow of heated air at the outlet of 368 flows either 1) through the heating aperture 364 in which the suture 304 is intermittently stopped and positioned during a tipping operation, or 2) alternatively the heated air is dumped into the surrounding atmosphere through a diverter channel 372, illustrated in FIG. 13(b). The flow of hot air is controlled by an air cylinder 374, under control of a solenoid 376, which controls the flow of actuating air through air tubes 378, 380. The air cylinder 374 controls the position of a retractable slide element having a flow aperture therein which is selectively positioned in front of either 1) a channel into the heating aperture 364 or 2) the diverter channel 372, depending upon the position of the slider element which is controlled by an air cylinder.

As an example, the following control parameters have been established for heat tipping of Braided VICRYL sutures sizes 1, 0, 2/0, 3/0 and 4/0. The suture tension refers to the tension force in grams which the tension roller 314 and torque motor 316 apply to the suture as it is being drawn through the machine by the grippers.

| Suture Size | Tipping Temp. +/−25 deg. | Tipping Time +/−25 Ms | Suture Tension +/−25 Grams |
| --- | --- | --- | --- |
| 4/0 | 375 F. | 380 | 275 |
| 3/0 | 395 F. | 380 | 275 |
| 2/0 | 410 F. | 380 | 275 |
| 0 | 425 F. | 380 | 275 |
| 1 | 435 F. | 380 | 275 |

As a further example, the following control parameters have been established for suture tension and heat tipping of silk sutures sizes 2/0, 3/0 and 4/0. In the following table the left column lists commercial needle types, the next column needle sizes, the next column suture sizes, the next column suture tension in grams applied by the tension roller 314, the next column tipping dwell time, the next column tipping heated air flow in standard cubic feet per minute, and the right column suture tipping temperature.

SILK SUTURE AND TIPPING PARAMETERS

| Needle type | Wire Size (0.000") | Suture Size | Suture Tension (grams) | Tipping Dwell (seconds) | Tipping Air Flow (SCFM) | Tipping Temperature (° F.) |
|---|---|---|---|---|---|---|
| Tolerance | N/A | N/A | (±10 grams) | (±0.020) | (±5) | (±15) |
| CT-1 | 39 | 2-0 | 275 | 0.380 | 190 | 300 |
| CT-2 | 39 | 2-0 | 275 | 0.380 | 190 | 300 |
| SH | 26 | 2-0 | 275 | 0.380 | 190 | 300 |
| SH | 24 | 3-0 | 275 | 0.380 | 190 | 300 |
| SH | 22 | 4-0 | 275 | 0.380 | 190 | 300 |
| SH-1 | 22 | 3-0 | 275 | 0.380 | 190 | 300 |
| SH-1 | 18 | 4-0 | 275 | 0.380 | 190 | 300 |

The previous tables are for braided VICRYL suture and silk suture, and similar tables could be developed for other suture materials such as Ethibond® (braided polyester) and monofilament and braided nylon.

The suture drawing, tipping and cutting is more completely described in U.S. Ser. No. 08/803,573, the parent application U.S. Ser. No. 804,477, and U.S. Ser. No. 08/804, 478, all of which are entitled "Suture Cutting System," the disclosures of which are incorporated herein by reference thereto.

The Swage Dial Drive Assembly

Figure 7A:
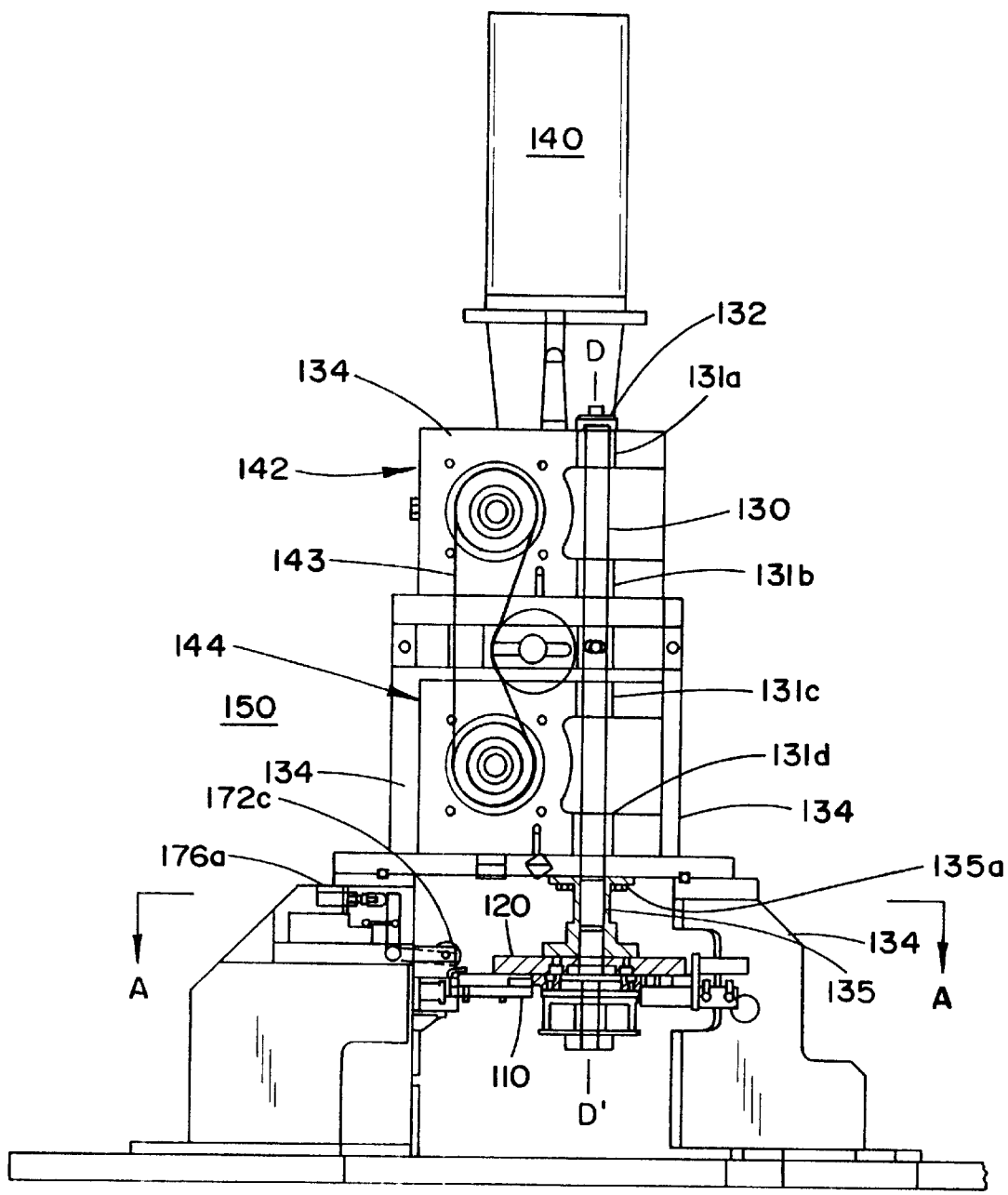
FIG. 7(a) is an elevation view of a portion the apparatus illustrating the inventive drive for the cam dial and swage dial of the present invention.
Figure 7B:
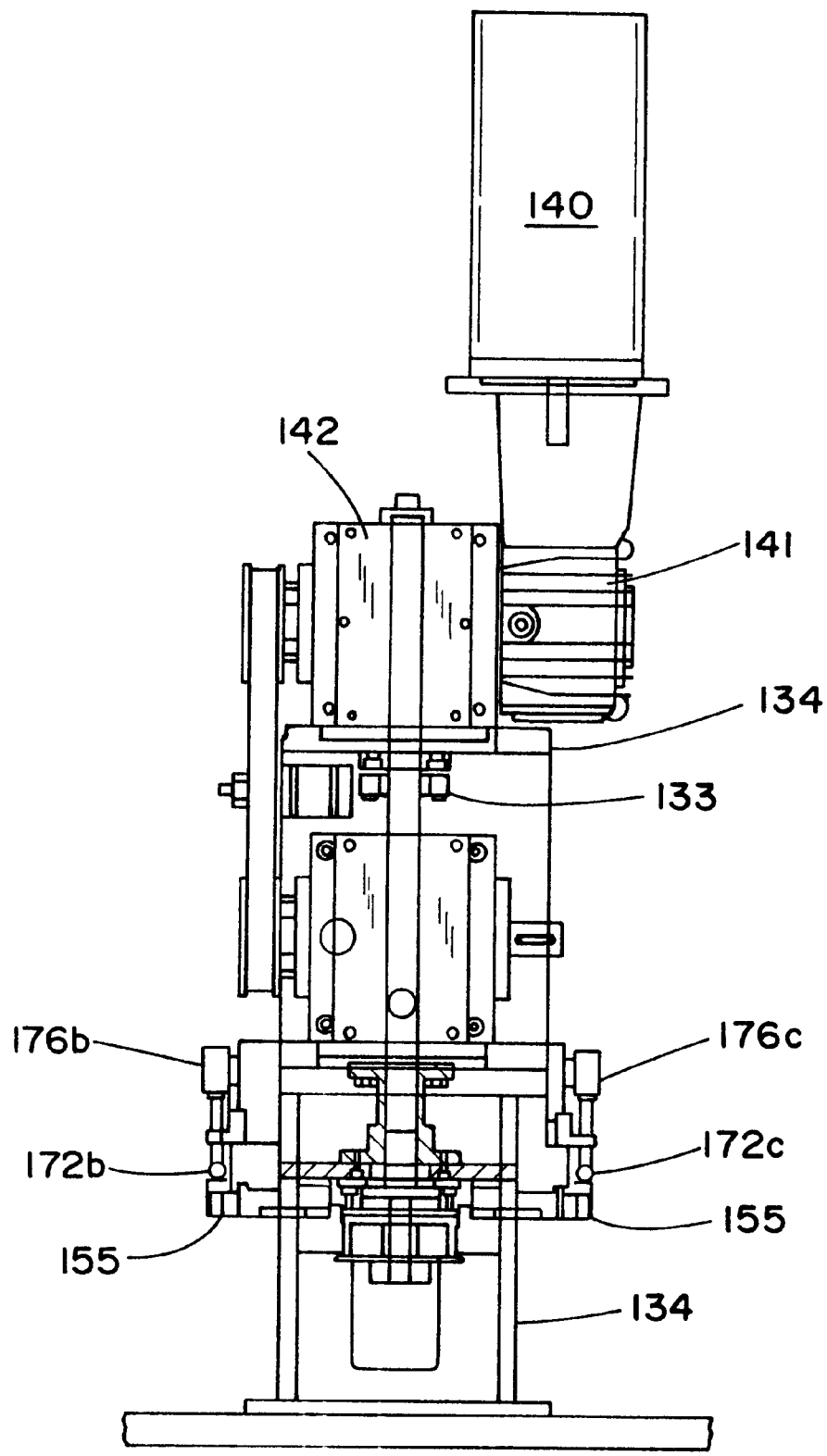
FIG. 7(b) is a side view of the drive for the swage dial illustrated in the elevation view of FIG. 7(a).
Figure 8:
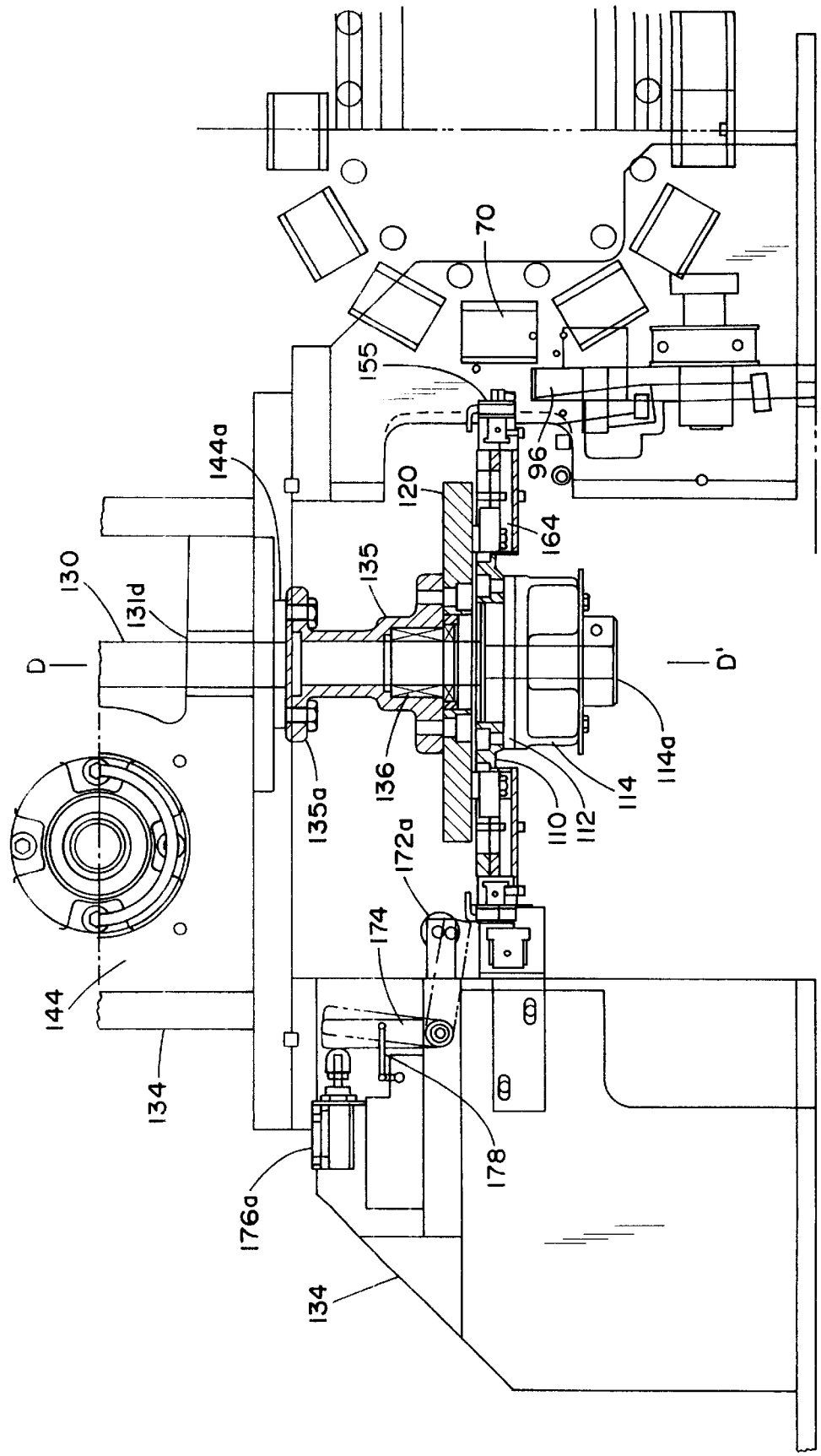
FIG. 8 is a detailed and partially cross section view of the drive for the swage dial taken along section lines "A"—"A" in FIG. 7(a) which illustrates a universal gripper ready to reciprocate outwardly to receive an oriented surgical needle from a precision conveyor.

The drive assembly for the swage dial 150 is illustrated in FIGS. 7a, 7b and 8. As illustrated in FIG. 7a, the swage dial assembly 150 includes a swage dial 110 and a cam dial assembly 120 both of which are independently driven by the drive means of the present invention. A drive motor 140 drives both of these dials through a first indexing drive transmission 142 and a second indexing drive transmission 144 through a 90° reduction transmission 141 and are coupled together with a timing belt 143. The indexing drive assemblies 142,144 are "CAMCO" Indexer Drivers Model 350RGD 4H24-360 with a 10 to 1 reduction in transmission 141 and an oscillation motion for the cam dial assembly 120. As will be hereinafter explained with respect to FIGS. 10–11, the first indexing CAMCO drive includes 180° of drive and 1800 of dwell for every revolution of the transmission drive 141 which results in a 90° drive dwell cycle for the first indexing drive 142. The first indexing drive 142 drives shaft 130 about a single drive axis D–D' illustrated in FIGS. 7–8. It is journalled for rotation in bearings 131a,b,c, and d and is secured in place by drive cap 132 and a compression drive collar 133 which is connected to the output of the first indexing drive 142. A modular frame assembly 134 supports each of the drive elements about the central drive axis D–D'.

The second indexing drive 144 also includes 180° of drive, a second 60° of drive, a 30° dwell, a 60° drive and a 30° dwell for each revolution of the input drive from belt means 143, and the indexing drive 144 is phased with the drive and dwell cycles of the first drive 142. As will be hereinafter described with respect to FIGS. 10 and 11, during each dwell period of the swage dial 110, the cam dial assembly 120 is held in a dwell position and then rotated to enable radial reciprocation of the universal grippers with respect to the swage dial 110.

The cam dial assembly 120 is mounted on an annular drive collar 135 which connects the output of the second indexing drive 144 to the cam dial plate 120 as more fully illustrated in FIG. 8. The annular drive 135 is journalled for rotation on drive shaft 130 by means of needle bearings 136 to provide a single drive access D–D' for rotation of the swage dial assembly 150. The annular drive collar provides suspension support and rotational drive for the cam dial assembly 120. The use of this annular collar also separates the cam dial and swage dial from the drive apparatus and enables operator workspace for alignment of the apparatus and for part changes when necessary. The annular drive collar 135 is bolted to the output drive flange of the indexing drive 144 as shone at 135(a).

The swage dial 110 is mounted for rotation on a ball detent clutch 114 which is fixably attached to shaft 130 and enables breakaway rotation between clutch drive plates 112 and 114 in the event of a catastrophic jam. The clutch 114 and shaft 130 also provide suspension support and rotational drive for the swage dial 110.

The annular cam drive 135 is bolted to the output of the second indexing drive 144 as illustrated at 135a and thus provides for both suspension support and rotation of the cam dial assembly 120. Likewise, the breakaway clutch 114 provides physical support and rotational drive for the swage dial 110 by virtue of its fixed mounting on shaft 130 at 114a.

The Swage Dial

Figure 14A:
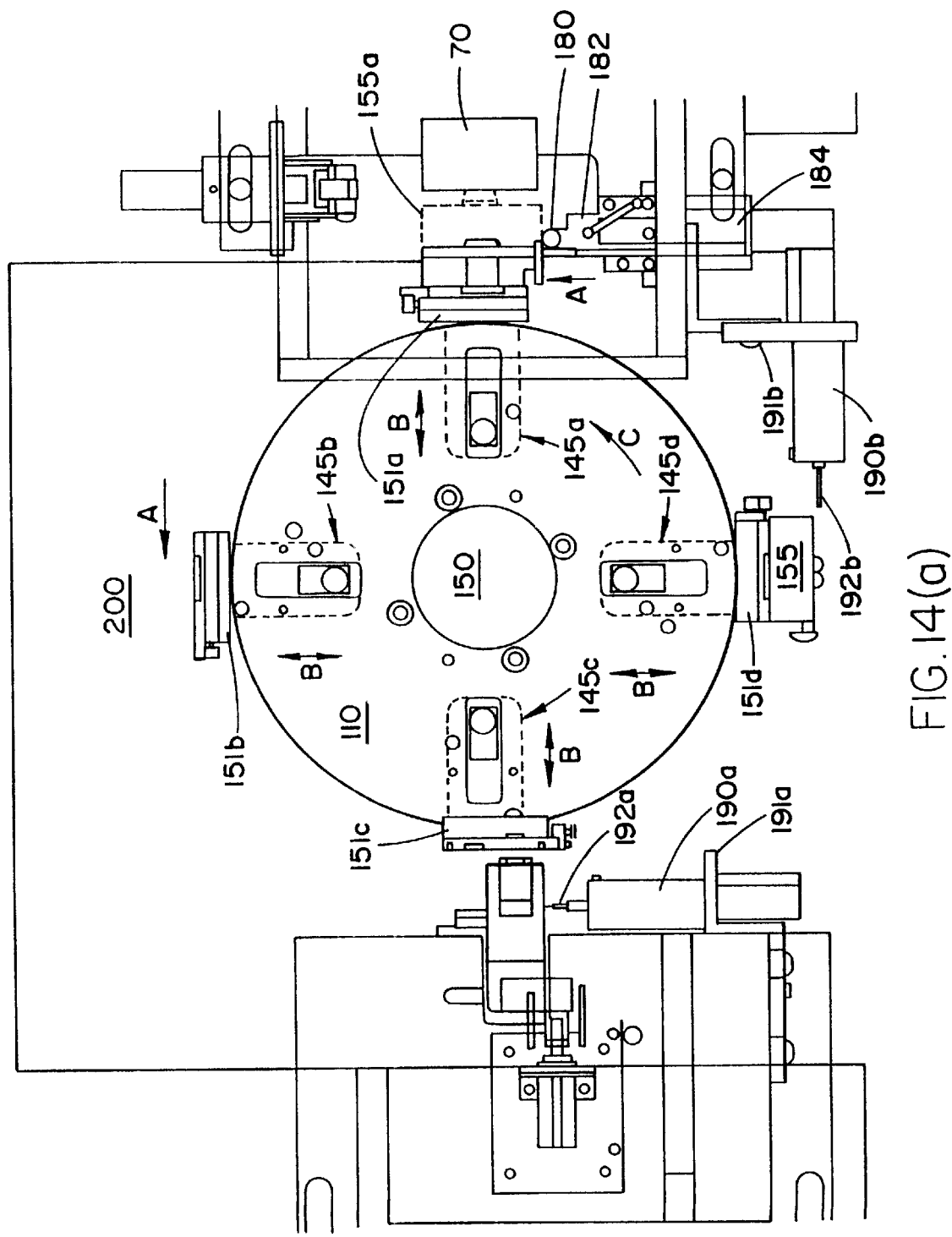
FIG. 14(a) is a top view of the swage dial assembly 150 comprising a swage dial plate 110 having four universal gripper stations 145a,b,c,d mounted thereon.
Figure 14B:
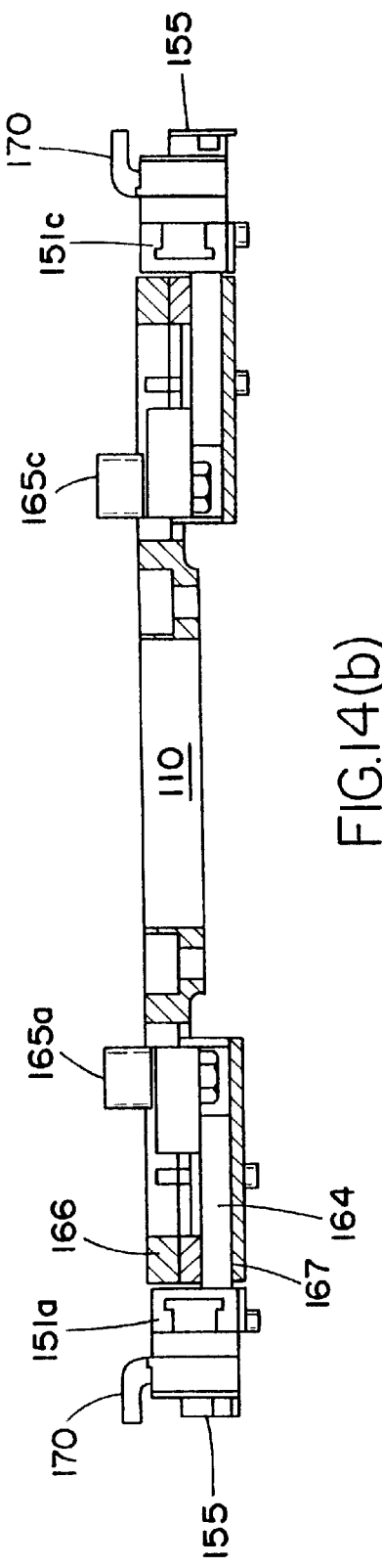
FIG. 14(b) is cross-sectional view of the four station swage dial assembly 150 showing universal gripper 155 in a retracted position.
Figure 14C:
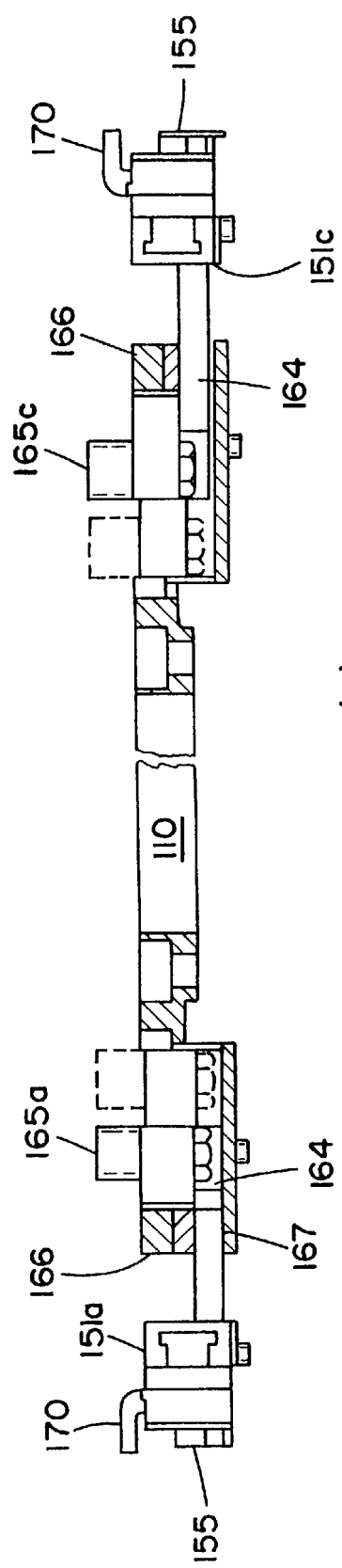
FIG. 14(c) is cross-sectional view of the four station swage dial assembly 150 showing universal gripper 155 in an extended position.
Figure 15A:
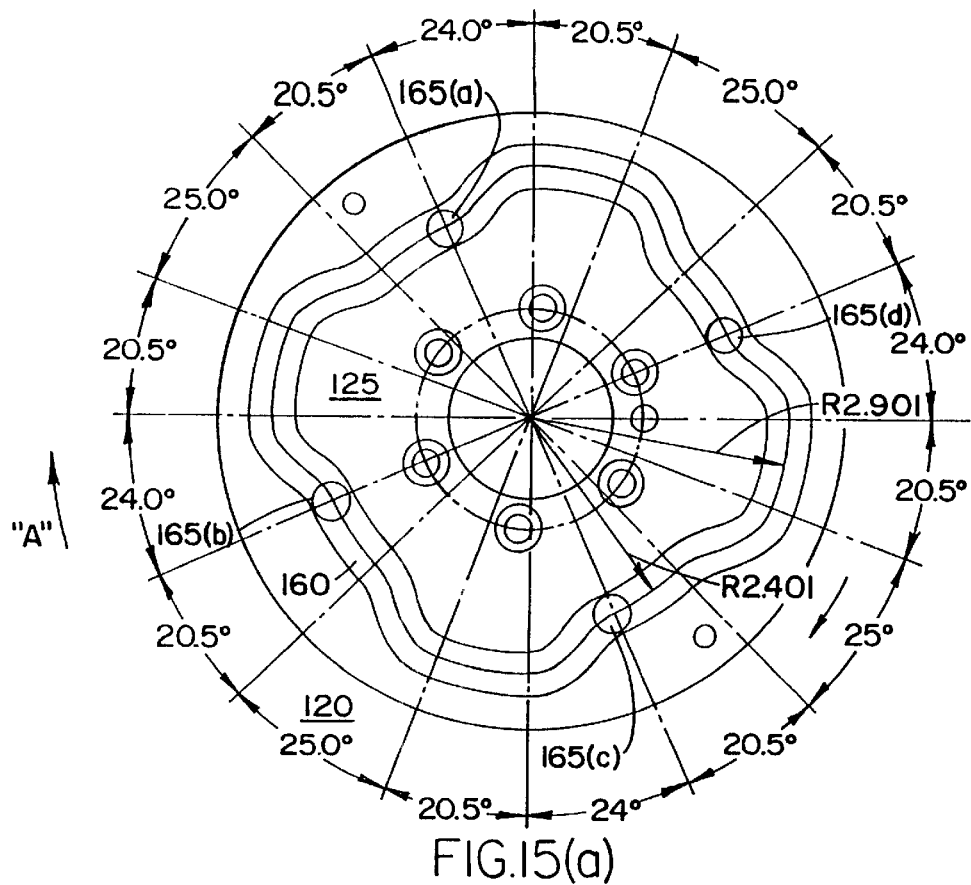

The process for extending each universal gripper 155 for needle processing at each of the stations 100, 200, 400, and 500 will now be explained. As shown in FIGS. 14(a), 14(b) and 14(c), each universal gripper 155 is connected to a reciprocating carriage 151 and a cam slide 164. Cam followers 165(a), (b), (c) and (d) are mounted to a cam slide 164 at one end thereof with the universal gripper at the other end. Cam slide 164 is slidable within stationary guides 166,167 and is adapted for reciprocal movement when the cam follower 165 is actuated. In the preferred embodiment shown in FIG. 15(a), cam followers 165(a)–(d) are rollers that fit within the cam track of a rotatable cam dial assembly 120. Cam dial assembly 120 is shown in FIG. 15(a) as comprising a cam dial plate 125 having a continuous cam tracks 160 which receives cam followers 165(a)–(d) attached to universal grippers 155a,b,c, and 155d, respectively. Each cam follower 165 is positioned within the cam track at each station for movement therein.

Figure 15B:
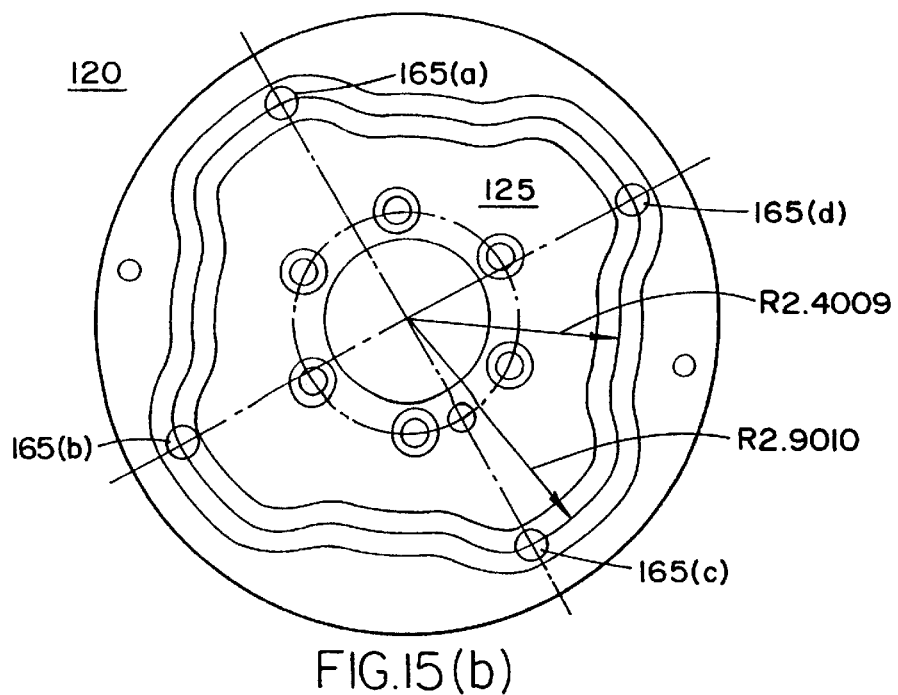

As illustrated in FIG. 15(a), cam dial 125 is positioned above swage dial 110 and mounted coaxial therewith. The cam dial 125 is rotatable about a central axis and controlled by a separate rotary indexing transmission as described previously so that it may rotate separately from the swage dial plate 110. The cam dial is driven in multiple drive and dwell cycles as previously explained, and the degrees of each phase are diagrammatically illustrated in FIG. 15(a). FIG. 15(a) also shows cam followers 165a–d in a first retracted position within the cam track 160. When the dials are in this position, each of the reciprocating carriages and consequently universal grippers 155 are in their retracted position as shown in FIG. 14(a) and 14(b) discussed above. To extend the universal grippers 155 in place at their respective stations, the cam dial plate 125 is rotated in the clockwise direction with respect to the swage dial plate 110, as indicated by the arrow A in FIG. 15(a), for approximately 25 to 45 degrees, forcing cam followers 165a–d in its cam track 160 to move toward the periphery of the dial as shown in FIG. 15(b). Consequently, each of the cam slides 164, reciprocating carriages 151a, and the universal grippers 155 move to the extended position as shown in FIG. 14(c). To move back to its retracted position, the cam dial plate 125 is rotated in the counter clockwise direction with respect to the swage dial plate 110 for approximately 20 to 30 degrees, forcing cam followers 165a–d in the cam track 160 to move to their retracted position (FIG. 15(a)). Consequently, the cam slide 164, reciprocating carriage 151a, and the universal gripper 155 move back to the retracted position as shown in FIG. 14(b) and discussed above.

It should be understood that when cam dial plate 125 rotates with respect to swage dial 110, each universal gripper 155 is either extended or retracted by the cam track. Thus, the system is designed so that all processes performed at each station occur simultaneously and for approximately the same duration of time when the universal grippers are in their extended position, for e.g., for needle pick-up, for needle swaging, or, for needle pull-testing.

When the universal gripper 155 is retracted, the needle engaged thereby may then be indexed to a different station for further processing. To index the needle to another station, both swage dial plate 110 and cam dial plate 125 are rotated together for approximately 90 degrees to position the universal gripper at the next station. For example, when the cam dial plate 125 and the swage dial plate 110 are simultaneously rotated 90 degrees counterclockwise in FIG. 14, the gripper 155 that had received the needle at station is now indexed to station 200 for swaging a suture thereto. Similarly, after swaging, the cam dial plate 125 and the swage dial plate 110 are simultaneously rotated counterclockwise so that the armed needle at station 200 is indexed to the pull-testing station 400 for pull-testing thereof. The operations performed concurrently at each station about the swage dial increases throughput to provide an output of pull-tested armed surgical needles at a rate of approximately 40 to 60 needles per minute or 20–30 double-armed sutures in the preferred embodiment.

Universal Gripper

As illustrated in FIG. 1, the rotatable swage dial assembly 150 cooperates with four stations where simultaneous needle operations are performed. In the detailed illustration of FIG. 14(a), the swage dial assembly 150 includes a swage plate 110 having four universal gripper stations 145a, 145b, 145c, 145d spaced equally thereon.

The swage plate 110 is rotatably mounted at a central hub 112 on a ball detent safety clutch 114 (illustrated in FIG. 8) and operable to rotate under the control of a control system computer 46. In the preferred embodiment, a separate reciprocating carriage 151 is provided at each universal gripper station of the swage dial assembly 150. For instance, as shown in FIG. 14(a), universal gripper station 145a includes reciprocating carriage 151a, while station 145b includes reciprocating carriage 151b, station 145c includes reciprocating carriage 151c, and station 145d includes reciprocating carriage 151d. Mounted to each reciprocating carriage 151a, b,c,d for retractable movement therewith, is one universal gripper 155, two of which are shown connected to gripper mounts 150(a) and (d) in FIG. 14(a).

As previously mentioned, each reciprocating carriage 151a,b,c,d and universal gripper 155 connected thereto is movable from a retracted position to an extended position. When the gripper 155 is in the retracted position shown in FIG. 14(b), the needle 39 may be conveyed to a different station as the swage dial rotates; when the gripper 155 is in the extended position as shown in FIG. 14(c), the needle is in one of the active stations, such as the automatic swaging station.

The universal gripper of the present invention receives the needle from the precision conveyor and moveable hard stop mechanism, and transports the needle through the swage operation in which a suture is automatically inserted into the barrel end of the needle, and the metal of the needle swaged about the suture. As can be appreciated, when the opening in the barrel is only 0.0106 and the suture diameter is 0.0088, a high degree of precision handling is required, particularly so when the insertion and swage operation need to be completed in approximately 0.5 seconds in order to maintain a 30 to 60 needle per minute cycle rate. The universal gripper also transports the needle through the pull test station in which the suture bond is tested and to the packaging area, where the armed suture (needle and suture assembly) is bundled with other armed sutures for future packaging.

In FIGS. 18(a) (b) and (c), both the slide portion 164 and the gripper portion of the universal gripper 155 are illustrated, with a pair of needle gripping jaws 146 and 148, each having a portion of a needle receiving indent 157 formed therein. Each of the jaws have a reciprocal slide portion 146(a), 148(a) formed as an integral part, which slides reciprocate in a channel 162 formed in housing member 174, The jaws 146 and 148 are biased to each other and to a closed position by a spring member 160. The jaws are opened by a pair of moveable pivot linkages 166, 168 which are mounted to and actuated by plunger 170, so that when plunger 170 is depressed, the linkages 166, 168 are moved outwardly, drawing the jaws 146 and 148 with them. The plunger 170 is actuated by a cam driven by an air motor at each automatic station to open and close the jaws about a needle 39.

In the apparatus, a plurality of universal grippers are employed, i.e., at least 2 and preferably 4, each of which grips a single needle at positioning, at swaging, at testing and at off-load, as previously described. As the universal gripper is moved into position, the jaws 146,147 are opened and the gripper is reciprocated towards the needle so that open jaws are presented on each side of the needle. The jaws of the precision conveyor boat 70 are then opened, and during transfer, the needle rests on the moveable hard stop 96. The jaws 146,148 of the universal gripper are then closed to grip the needle and the moveable hard stop 96 is reciprocated out of engagement with the needle, and away from the jaws of the precision conveyor to allow the precision conveyor to advance the next needle into the needle transfer position.

The step of loading of the individual precisely oriented surgical needle 39 from the precision conveyor boat 70 and the moveable hard stop 96 onto the universal gripper 155 at the precision loading station 100 involves a compound movement on the part of the universal gripper. Since the needle is gripped in detents formed in the jaws of the conveyor boat 70, and since one of the jaws of the precision conveyor boat 70 is fixed, it is necessary for the universal gripper to transcend a compound movement when removing the needle from the conveyor boat jaws. If a straight reciprocal movement is attempted, the needle is stripped from the jaws of the universal conveyor by the detent in the fixed jaw of the conveyor boat 70. This compound movement is found at both the precision position station 100 and the swage station 200, which also uses fixed and moveable jaws. The use of a fixed jaw substantially improves the accuracy of the alignment of the needle with the suture at the swage station.

In the frontal view of the universal gripper as shown in FIGS. 15(a) and (b), jaws 146 and 148 of the universal gripper 155 extend perpendicularly from the gripper to engage the barrel end 44 of the arcuate needle 39.

FIGS. 19(a), (b) also illustrates two roller cam surfaces 172, 180 which act on the universal gripper. A cam surface 172 is found at each of the four stations, (Precise positioning, swage, test and off-load) and is used to open jaws 146 and 148 of the universal gripper at each station. FIGS. 7 and 8 also illustrate three pneumatic drives 176 (a), (b) and(c) which actuate rollers 172 (a), (b) and (c) to open and close the jaws of the universal gripper 155 as will be hereinafter explained in greater detail.

FIG. 8 illustrates a typical positioning for cam 172 above the needle pull test station, wherein cam roller 172(a) is mounted on a bell crank 174, which is actuated by an air cylinder 176(a). The cam 172(a) is normally biased to a non-engaged position by spring 178.

Each of the universal grippers 155 is mounted for linear movement with respect to the cam slide 164 by means of an off-set slide assembly, the details of which will be explained as with respect to FIGS. 14(a), (b) and (c). As indicated therein, the housing 174 of the universal gripper is mounted on a mounting block 175 and slide 177, and slide 177 is spring biased to a home position during reciprocation within slide carriage 151 by spring member 179. This second reciprocal movement is transverse to the reciprocal movement imparted by cam slide 164.

Referring to FIGS. 19(a), (b), roller cam 180,180(b) are used to provide the compound off-set movement of the universal gripper as it is reciprocated outwardly by the swage dial cam plate 125. FIG. 14(a) illustrates a typical positioning for the off-set drive used to drive cam roller 180 at the precise positioning station 100. Roller cam 180 is mounted on a linear slide 182, which is driven by an air motor 184, mounted on the swage dial frame. FIG. 14(a) also illustrates the relative motions of the universal gripper 155, with arrow A indicating the off-set movement, arrow B indicating the reciprocal movement which results in the radial reciprocation of the universal gripper 155 to 155a in FIG. 14(a), and arrow C indicating the rotary motion of the swage dial 110.

To accomplish the transfer of the needle to a universal gripper 155, the universal gripper 155 is extended and translated horizontally so that the face of the universal gripper is adjacent to the needle precision conveyor boat 70 as shown in FIGS. 8 and 10(a). In this position, the jaws 146 and 148 penetrate the plane of the needle 39 on either side thereof. A load solenoid or similar device depresses a pusher arm of the precision conveyor boat 70 to release the needle from the engagement jaws 77,79 of the precision conveyor boat 70 so that it rests on the movable hard stop assembly between jaws 146 and 148 of the universal gripper 155. Simultaneously therewith, as controlled by the control system computer, jaws 146 and 148 are actuated from the non-engaging position to an engaging position to thereby engage the needle 39 in an oriented position as shown in FIG. 19(a). The universal gripper 155 is then off-set horizontally and retracted radially and the swage dial assembly 150 is rotated to the swaging station 200 to accomplish automatic swaging of the suture to the needle 39.

Needle Swaging Station

The swaging operation taking place at the swaging station will now be described with reference to FIG. 16, FIGS. 18(a)–(c) and FIGS. 19(a)–(b). FIGS. 19(a)–19(b) illustrate the universal needle gripper 155 and swaging and suture alignment dies shown in two stages of the suture insertion and needle swaging sequence. This sequence, and the interaction of the dies in relation to each other, the needle, and the insertion of the suture, accomplish the insert and swage function with minimal parts changes for each group of needle diameters and simple motions.

Figure 16:
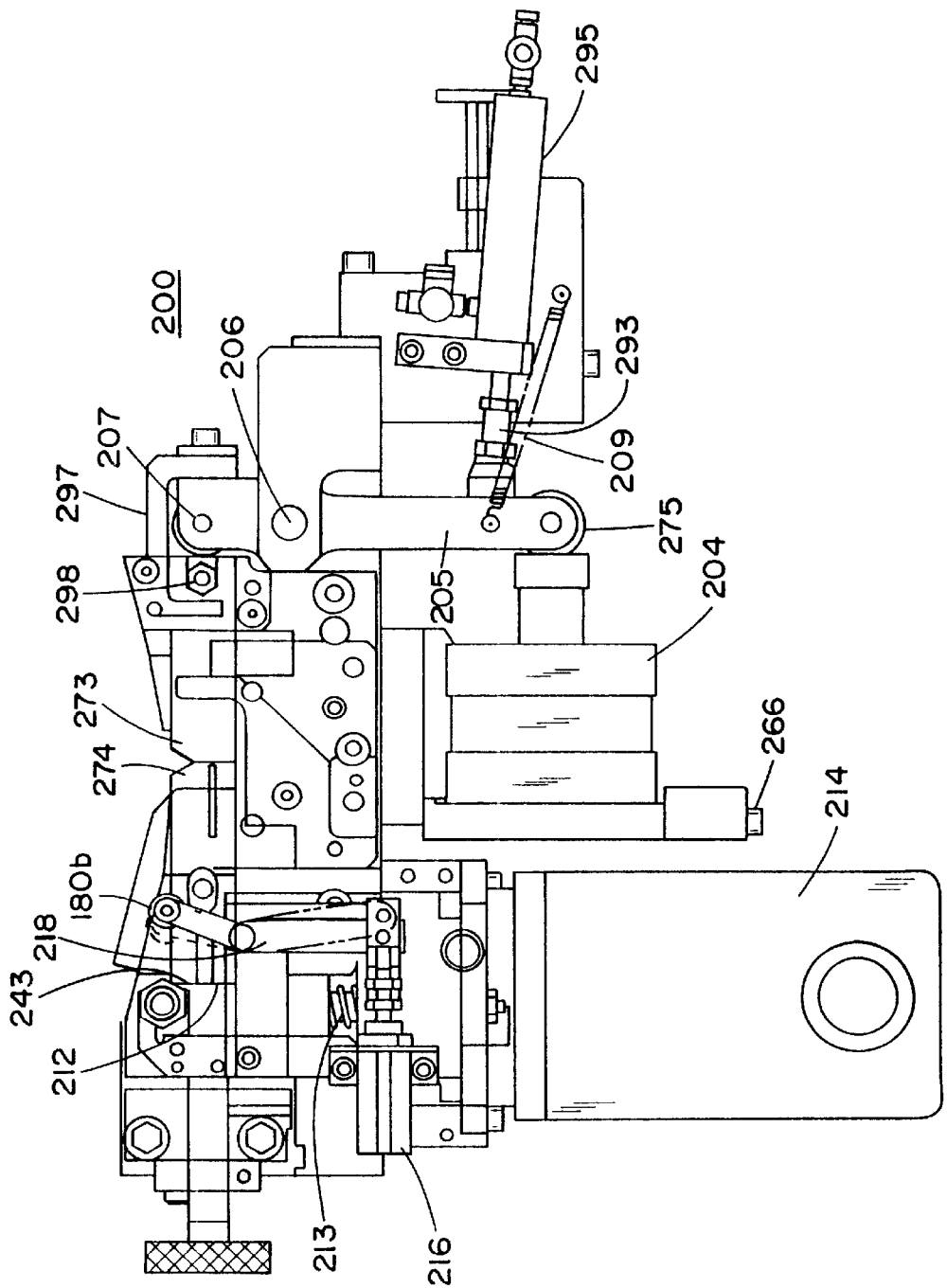
FIG. 16 is a top plan view of the swage assembly and off-set assembly of the present invention used for swaging the needles for suture attachment.

After conveying the needle to swaging assembly 200 shown in FIGS. 16 and 19(a), the universal gripper 155 is radially extended from the swage dial, and off-set to the side in the manner described above to position the suture receiving end 44 of needle 39 between the funnel shaped die opening formed at the ends of two swage dies 273,274 as shown in FIG. 19(a). As will be explained, swage die 274 is relatively fixed in position and swage die 273 is movable laterally toward the fixed swage die 274, as indicated by the arrow "A", to accomplish swaging of the suture receiving end of a needle placed therebetween. A funnel shaped die opening having an exit diameter slightly larger than the diameter of the suture receiving end 44 of the needle is formed when the two swage dies 273,274 are positioned adjacent each other as shown in FIGS. 15(b).

In the preferred embodiment shown in FIGS. 23(a) and 23(b), the ends of each of the swage dies 273,274 are provided with rectangular die cavities 283,284 respectively, to permanently swage the suture to needle 39. Note that as illustrated in FIGS. 23(a), (b), The swage dies are for a small 18 mil needle, and FIG. 23(a) has been magnified 2 × and FIG. 23(b) magnified 100× for purposes of illustration. Different sets of swage dies may be provided, depending upon the size (diameters) of the needles and sutures to be swaged, and in the practice of the present invention, dies for needles ranging from 18 mil (0.018) to 50 mil (0.050). The die cavities illustrated in FIGS. 23(a), (b) are rectangular in shape with a 90 degree angle, and used to impart a permanent swage bond between needle and suture. Similar dies may be used with round die faces to impart a controlled release swage bond between the needle and suture.

To precisely position the suture receiving end 44 of needle 39 between the swage die opening formed at the ends of two swaging dies 273,274, the movable swage die 273 is temporarily moved apart. In the illustration of the swaging assembly 200 shown in FIGS. 16 and 19(a), swage die 273 is moved apart from the fixed swage die 274 by actuating air cylinder 295 to provide a force upon cylinder rod 293 to enable swage die operating lever 205 to pivot about pin 206 and pull a retraction arm 297 which engages stud 298 affixed to moveable swage die 273 a predetermined distance away from the fixed swage die 274. In the preferred embodiment, lever 205 is biased by spring 209 so that the movable swage die 273 will return toward the fixed swage die by the spring restoring force when the pressure provided by the air cylinder 295 is terminated.

FIG. 19(a) shows die 274 in its fixed position, and moveable die 273 in its spaced apart position prior to receiving the surgical needle 39 presented by universal gripper 155. Suture alignment die 270 containing suture guide funnel half 270(a) is positioned under swage die 273, and free to slide laterally within limits. Suture alignment die 270 has a tang 270(b) that protrudes into cavity 273a formed within swage die 273. Compression spring 273c bears against the back wall of cavity 273a and tang 270(b) such that funnel die 270(a) slides forward until it is constrained by the inner wall of cavity 273(a). In this position, it is forward of the center axis defined by the suture receiving end of the needle, and serves as a shelf that helps assure suture receiving end 44 of needle 39 is in position for swaging. In this stage of the cycle, the parts are not positioned for suture insertion, and suture clamps 365(a), (b) gripping suture 304 and stiffened end 358, are in dwell. Suture alignment die 271, containing funnel half 271(a), is fastened to swage die 274 by suitable fastening means.

While the swage dies are apart, the universal gripper 155 is extended to position the suture receiving end 44 of needle 39 within the swage opening as shown in FIG. 19(a). Referring to FIG. 16, the universal gripper is off-set during entry and egress by cam roller 180(b), which is driven by air cylinder 216 through bell crank 218. This off-set is necessary to allow the needle to box step into the swage die opening 284 in the fixed swage die as it is placed in position by the universal gripper 155. After positioning the suture receiving opening 44 of needle 39 at the swage die opening 284, the moveable swage die 273 is moved toward needle 39 with the resilient spring force present in spring 209 that is sufficient to enable the dies 273,274 to grip and locate the suture receiving end 44 precisely against fixed swage die 274 without deforming the cavity of the suture receiving opening 44 formed therein. Concurrently, the jaws 146,148 of universal gripper 155 are opened by downward external force on plunger 170, by cam roller 172 as described above, thereby releasing the needle so that its position is determined by the grip of swaging dies 273 and 274. The motion of dies 273 and 270 causes the face of suture alignment die 270 to come in contact with the corresponding face of suture alignment die 271. The resilient force causing this motion is forceful enough to compress spring 273c, and move funnel die 270(a) to the left, such that tang 270(b) is no longer in contact with cavity wall 273(a). Dimensioning of dies 270 and 271 is such that this motion results in the formation of two funnel halves 270(a) and 271(a) defining a smooth conical shape that is coaxial with the suture receiving end 44 of needle 39.

FIG. 19(b) illustrates suture grippers 365(a), (b) moved vertically to the insertion position, which causes stiffened suture end 358 to enter the funnel defined at 270(a), 271(a), and be guided into the suture receiving cavity 44 of needle 39 axially aligned therewith. Note that the exit diameter of the conically shaped funnel guide formed of funnel halves 270(a) and 271(a) is preferably equal to or greater than the diameter of the suture tipped end 358 and smaller than the diameter of the suture receiving end 44 of the needle 39, so that the tipped end 358 of the suture strand may be easily inserted therein. An enlarged detail of the suture alignment dies 270,271 and the placement of the funnel portions 270(a) and 271(a) is illustrated in FIG. 19(b). Once the strand is inserted into the suture receiving end 44 of the needle (step 27) as discussed above, the automatic swaging of the suture receiving cavity occurs.

In the preferred embodiment of the swaging assembly 200 shown in FIG. 16, a pneumatic air cylinder 204 provides air pressure to actuate cam 275 that bears on lever 205 to pivot about pivot point 206 and drive cam 207 against the end of the moveable swage die 273 to thrust movable swage die 273 toward the fixed swage die to accomplish the swaging of the suture receiving end of the needle placed therebetween. Air pressure is supplied to the swage cylinder 204 via ports 266 under the control of the control system computer 46.

After the swage die 273 has been driven to a fixed stop by the swage cylinder, the suture receiving end 44 of needle 39 has been deformed to the desired shape defined by the swage die contours, as illustrated in FIG. 19(b). As deformation takes place, the moveable swage die 273 comes to a stop as a swage stop post which is press fit into the moveable swage die 273 strikes a reference wall cross milled into the frame of the swage assembly. When the swage stroke is performed, the swage cylinder drives the die and post assembly to the left (in FIG. 16) until it is positively stopped by the lower portion of post striking the wall of the cross milled groove in the assembly frame (located under swage die 273 in FIG. 16). This stalls air cylinder 204, so that the stroke of the moveable right hand die assembly shown is always the same for repeated cycles of the machine. In an alternative embodiment, both swage dies 273,274 may be movable towards each other to accomplish swaging.

In the preferred embodiment, the degree of swage compression imparted on the needle, and resulting strength of grip by the needle on the suture, is adjusted by precise positioning of the fixed die 274.

As shown in FIG. 16, servomotor 214 rotates a swage adjust screw 213. by driving a belt and reduction pulley on the end of swage adjust screw 213. The pitch of the swage adjust screw 213 is selected to move a sliding wedge 212 a small distance. The swage die 274 has a complementary ramp angle 243 at the opposite end which bears on the wedge 212 to retract or advance the position of the swage die 274 a precise distance proportional to the movement of the sliding wedge. Thus, the rotation of the swage adjust screw 213 and motion of the sliding wedge 212, results in transverse movement of the swage die 274 to thereby finely adjust its fixed position. For example, when a larger suture is to be swaged to a needle, the position of the fixed die 274 may be moved further away from the suture drawing axis so as to provide the desired amount of deformation when the swaging pressure is applied to the needle by the movable swage die 273. In the preferred embodiment shown in FIG. 16, the control system computer 46 will send the appropriate signals to automatically direct the servomotor 214 to adjust the position of the swage adjust screw 213, and hence, the position of the fixed die 274, in accordance with the pull-out test values of the needle-suture bond as measured by automatic pull-test system as explained in further detail below.

Specifically, appropriate control signals may be generated to direct the servomotor 214 to adjust the rotational position of the swage adjust screw 213 in accordance with stored statistical results of the pull-testing occurring at the pull-test station. Automatic pull-testing of the armed needle is desirable to ensure that the upstream swaging dies are optimally positioned to avoid over-swaging the needle-suture bond and hence, preventing the likelihood of clip-off, and, to avoid under-swaging the needle-suture bond to prevent the chance of pull-out.

Referring to FIG. 19(a), after the needle has been swaged to the suture, the universal gripper 155 closes jaws 146,148 on needle barrel end 44 as the drive roller 172 is reciprocated out of engagement with plunger 170. Simultaneously therewith, the moveable swage plate 273 is retracted to enable movement of needle 39 by the universal gripper 155. Before the swage dial 110 is rotated, the offset drive cam roller 180(b) is again advanced to bear against cam plate 186 and provide egress of the needle 39 from the swage dye cavity in fixed swage plate 274. Once the universal gripper 155 and needle 39 have cleared the fixed swage plate, the cam dial assembly 120 is rotated advancing cam rollers 165 inwardly to retract the universal grippers 155 in a radial direction and enable rotation of the swage dial 110.

Swage dial 110 then rotates the first needle of the needle and suture assembly to a pull test station for testing as described in U.S. Ser. No. 08/847,132, entitled "Pull Test Station for Permanently Attached Sutures," also assigned to the assignee of the present invention, the disclosure of which is incorporated herein by reference thereto. While the first needle of the pair is being pull-tested, the second needle of the pair is swaged to the second end of the suture in the manner previously described with respect to the first needle of the pair.

Suture Cutter Assembly

Figure 24:
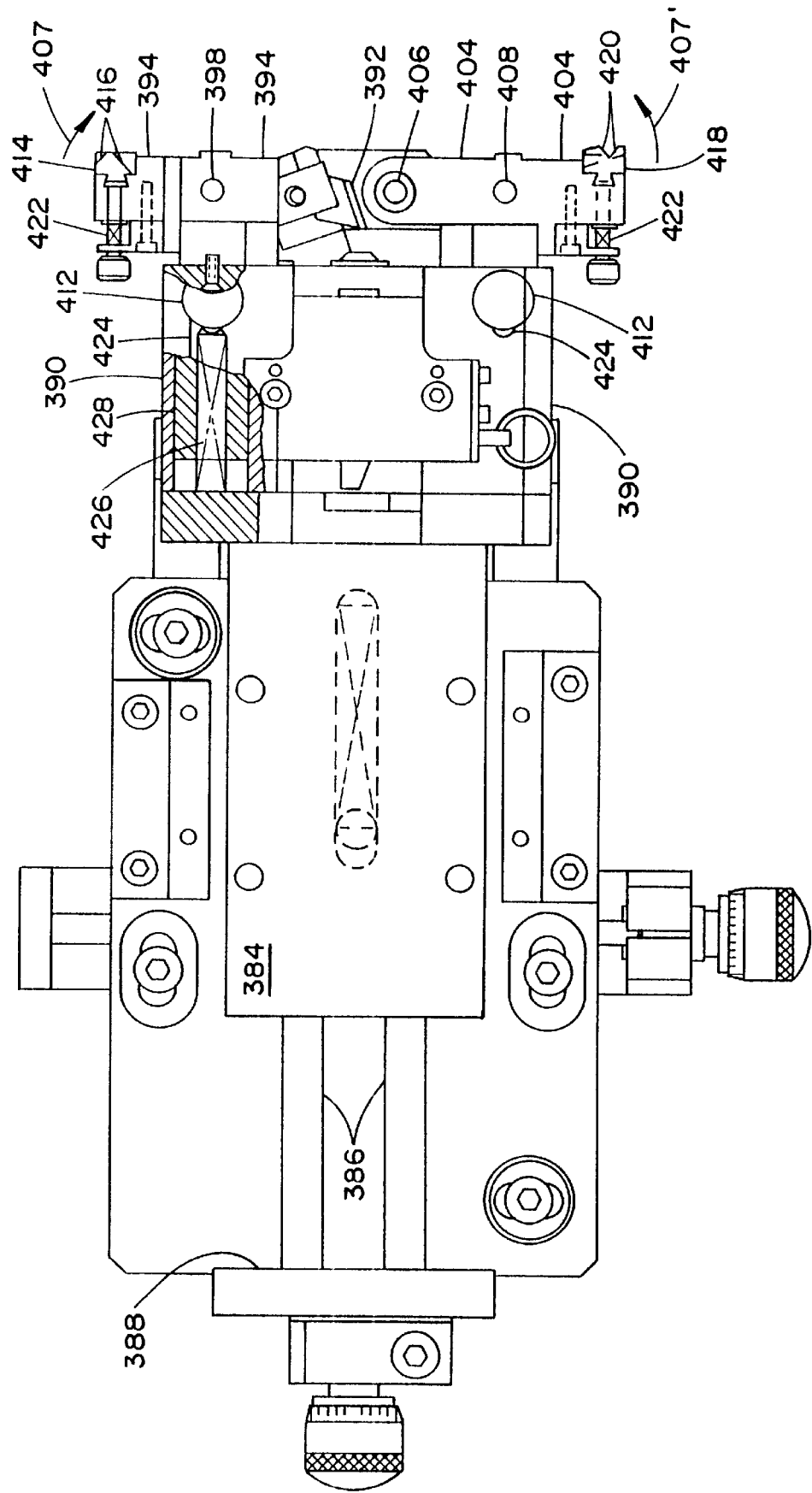
FIG. 24 is a top plan view of the cutter assembly of the present invention in a retracted position.
Figure 25:
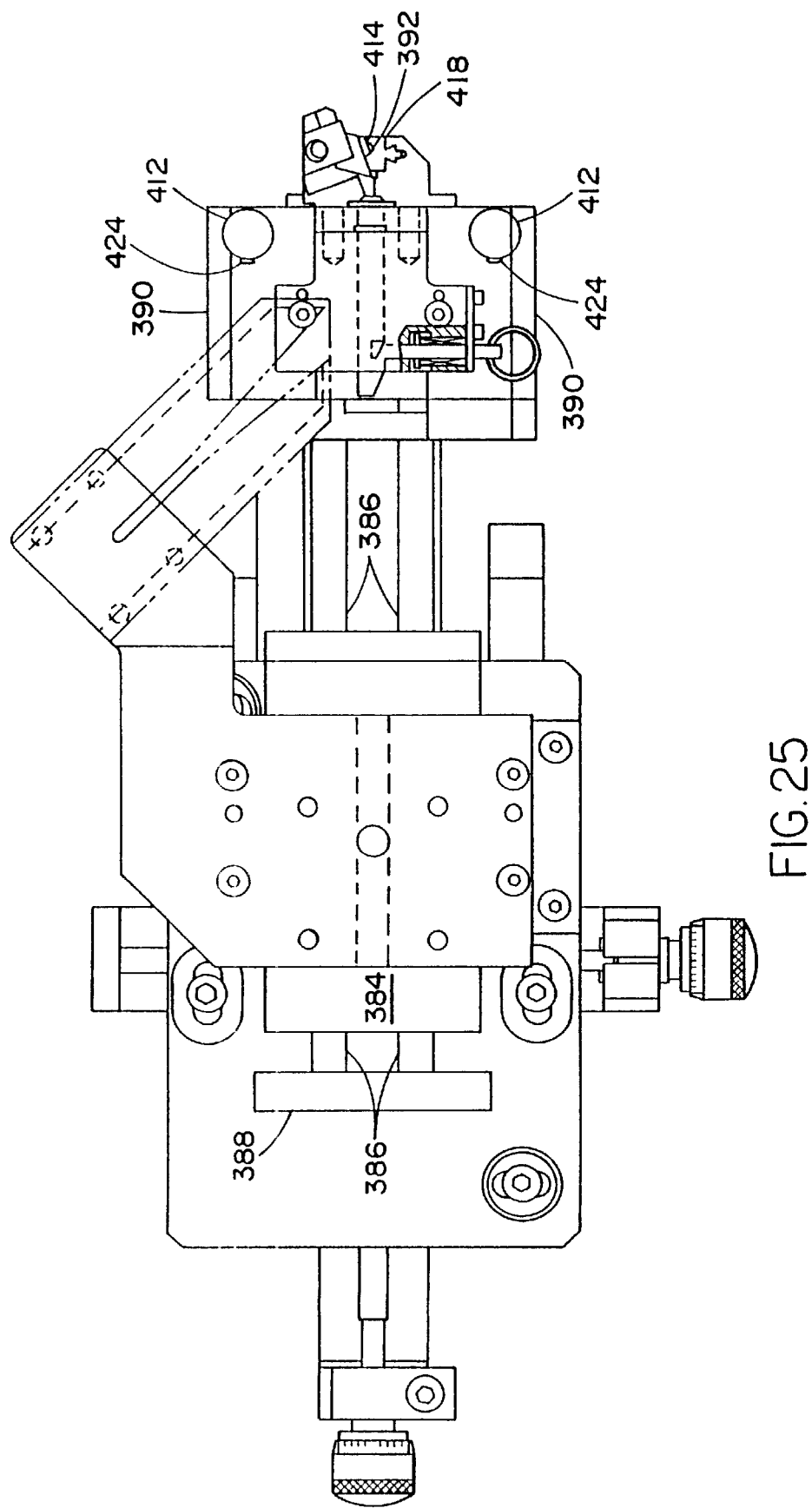
FIG. 25 is a top plan view of the cutter assembly depicted in FIG. 24 in an extended cutting position.
Figure 26:
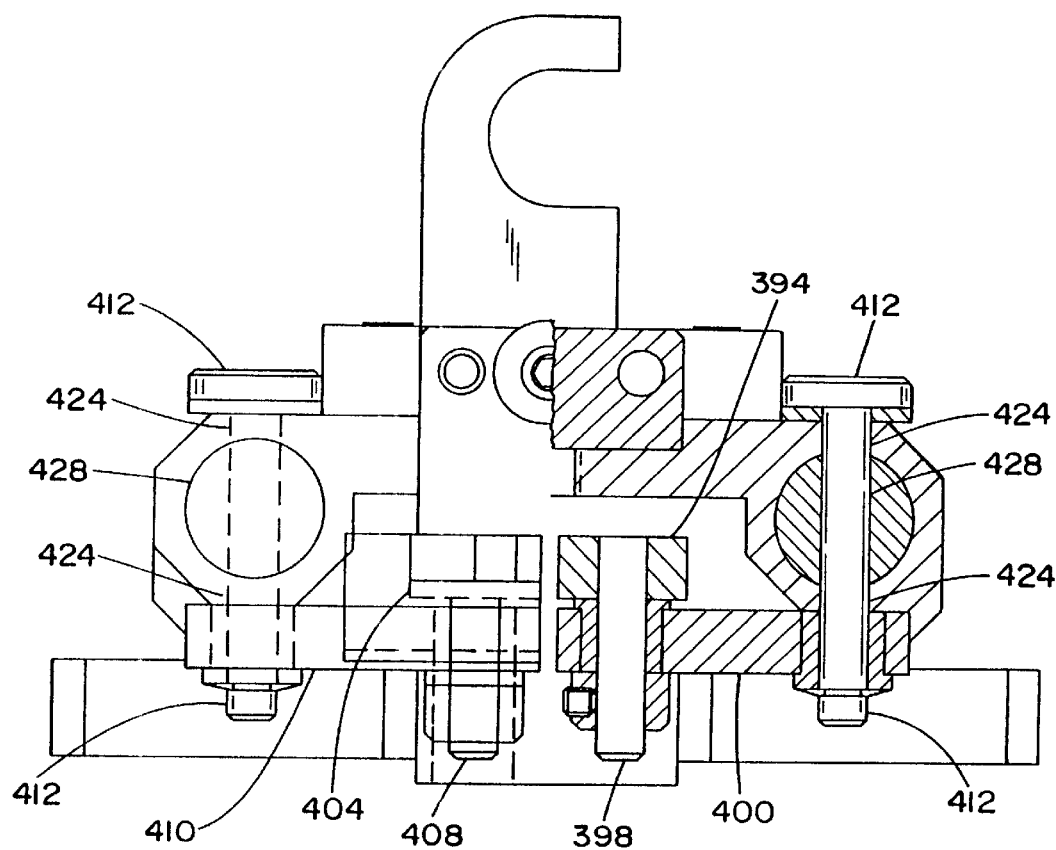
FIG. 26 is a front elevation view of the cutter assembly depicted in FIG. 24.
Figure 28:
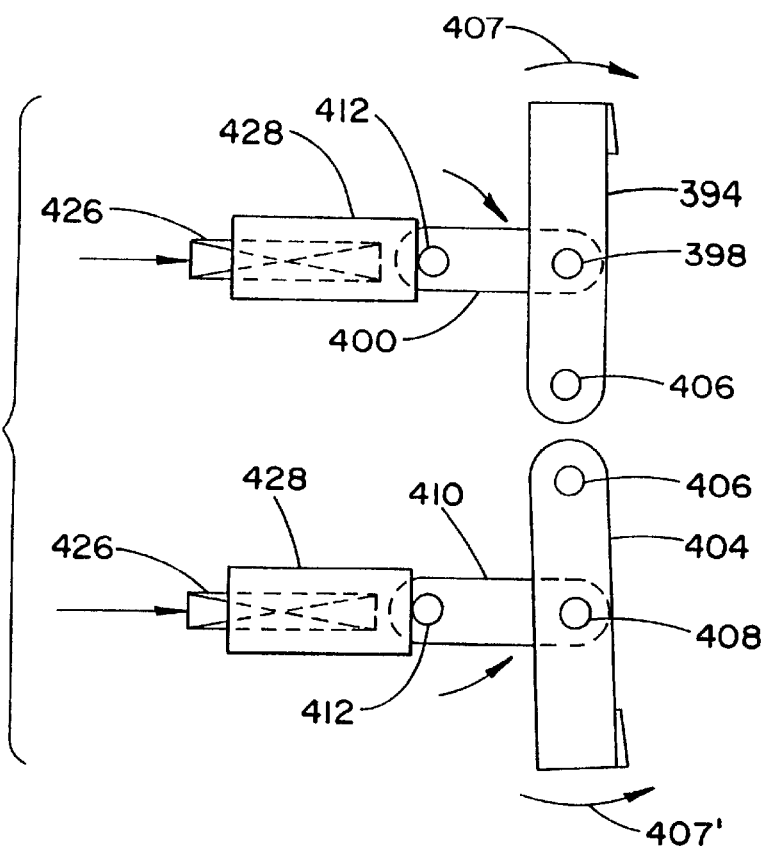
FIG. 28 is a simplified top planar view of the first and second locator arms, in a retracted position, as illustrated in FIG. 24.
Figure 29:
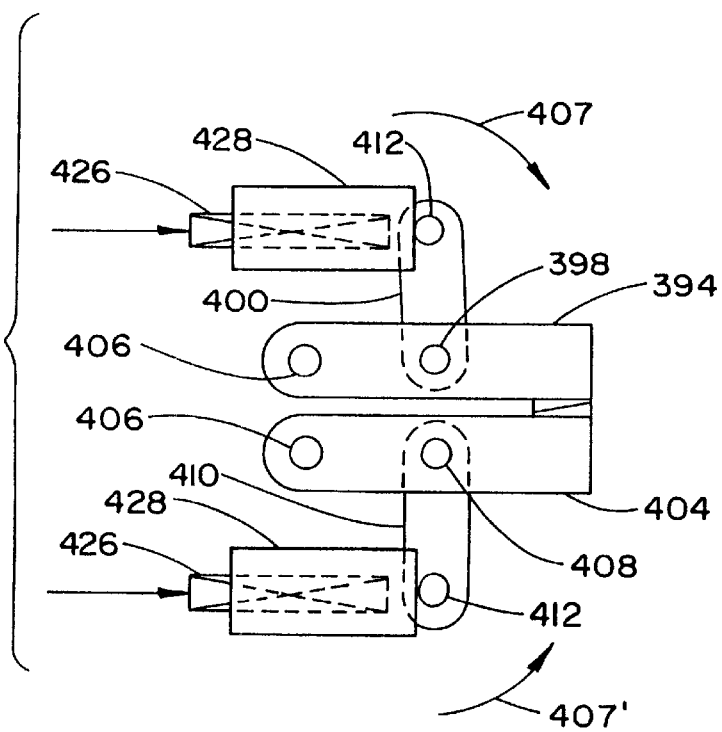
FIG. 29 is a simplified top planar view of the first and second locator arms, as driven by the first and second link arms to an extended, as illustrated in FIGS. 25 and 26.

FIG. 24 illustrates a top plan view of a cutter assembly pursuant to the present invention, shown in a retracted position. FIG. 25 is a top plan view of the cutter assembly of FIG. 24, shown in an extended cutting position. FIG. 26 is a front elevational view, similar to that of FIG. 9, partly in section, of the cutter assembly 334 of FIGS. 9 and 10, and illustrates further details of the drive mechanisms for the cutter assembly. FIGS. 28 and 29 are simplified top planar views of the first and second locator arms, with FIG. 28 illustrating the retracted position of FIG. 24, and FIG. 29 illustrating the extended position of FIG. 25.

The cutter assembly is actuated by an air cylinder 384 which during a cutting operation drives a slide mechanism (blade overtravel block) 390 from the retracted position of FIG. 24 to the extended position of FIG. 25. The air cylinder 384 mounts two drive rods 386 which extend therethrough and which the air cylinder translates back and forth to extend and retract the cutter assembly. A transverse bar 388 connects the two drive rods 386 at their ends remote from the cutter mechanism. The other ends of the two drive rods 386 are connected to the slide mechanism (blade overtravel block) 390, on which the knife blade 392 is mounted by a suitable mounting structure for movement therewith.

Referring to FIGS. 24–29, a first locator arm 394 is pivoted about a first stationary pin 406 at its inner end, and is pivotally mounted by a drive pin 398 to a first link arm 401 near its middle portion. Likewise, a second opposed locator arm 404 is pivoted about a second stationary pin 406 at its inner end, and is pivotally mounted by a drive pin 408 to a second link arm 410 near its middle portion. The second ends of the first and second link arms 401, 410 are secured to overtravel pins 412 which are mounted to the blade overtravel block 390, as illustrated in FIG. 26.

During operation, as the blade overtravel block 390 is driven by the air cylinder 384 from the retracted position of FIGS. 24,28 to the extended position of FIGS. 25,29, the overtravel pins 412 pull the first and second link arms 400, 410, which in turn push the drive pins 398, 408 of the first and second locator arms 394, 404 as illustrated best in FIGS. 26 and 28. This causes the first and second locator arms 394, 404 to rotate about the fixed pins 405, 406 as indicated by arrows 407, 407' in FIGS. 24 and 28 from the open position of FIGS. 24 and 28 to the closed position of FIGS. 25 and 29, and causes the first and second link arms to rotate to the position shown in FIGS. 25 and 29. The first locator arm 394 has a first insert 414 removably positioned at its end having a convex V shape 416, and the second locator arm 404 has a second insert 418 removably positioned at its end having a concave V shape 420. When the first and second link arms are rotated together as shown in FIG. 25, the convex V insert 414 clamps against the concave V insert 418 to secure the suture therebetween at the points of the Vs. The inserts are removable, and also secured in place, by set screws 422 in the link arms.

The overtravel pins 412 are not mounted fixedly to the overtravel block 386, but are mounted in elongated slots 424 in the overtravel block 390, and are mounted against spring-loaded piston 426,428 as shown in FIGS. 24, 28 and 29. After the locator arms 394,404 clamp against each other, further movement of the overtravel block 390 causes the overtravel pins 412 to compress the spring 426 loaded pistons 428 and translate in their slots 424.

During a cutting operation, as the air cylinder 384 drives the blade overtravel block 390 to the right from the retracted position of FIGS. 24 and 28 to the extended position of FIGS. 25 and 29, the first link arm 400 and locator arm 394 are driven in clockwise rotations as viewed in FIGS. 24–25, 28–29, as shown by arrow 407, and the second link arm 410 and locator arm 404 are driven in counterclockwise rotations as shown by arrow 407'. They are driven until the convex V insert 416 positioned at the distant end of the first locator arm 394 is seated into the concave V insert 418 positioned at the end of the second locator arm 404 to assume the position of FIG. 25, with the suture positioned and clamped between the points of the Vs of the inserts. The knife blade 392 is mounted on and is also driven to the right by the blade overtravel block 390 to assume the position shown in FIG. 25. Further movement to the right by the blade overtravel block 390 causes a compression of the springs 426 positioned behind the pistons 428, such that the inserts 416, 418 and clamped suture are now stationary. However, further movement to the right by the blade overtravel block causes the knife blade 392 to continue to translate to the right relative to the then-stationary positioning inserts 416, 418 and to sever the suture held therebetween. The cutting blade 392 translates along the side surfaces of the inserts, as best illustrated in FIG. 27, and cuts the suture.

Figure 27:
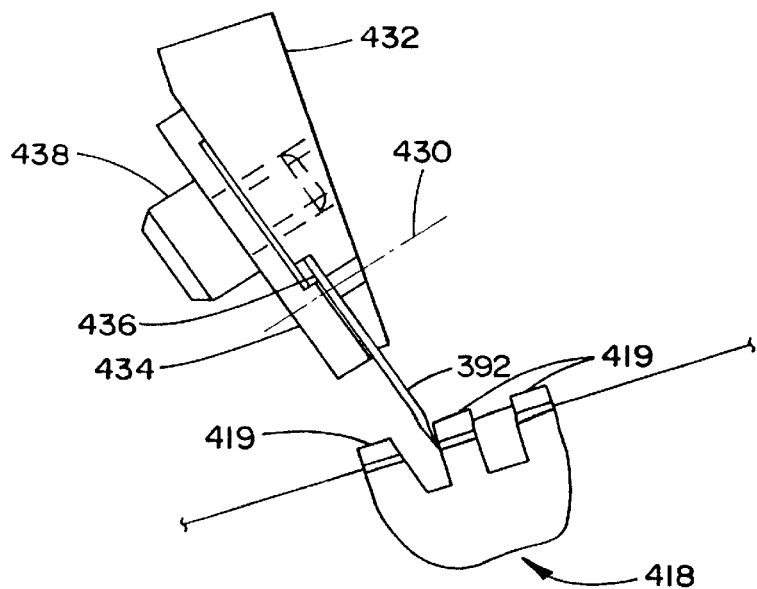
FIG. 27 is an enlarged detail of the cutting blade and suture positioner of the cutting assembly of FIG. 25 illustrating their relationship to a suture to be cut.

FIG. 27 illustrates a side profile of the concave V insert 418 which has three separate concave V arms 419 to position the suture. The convex V insert has three similar separate convex V arms, and the knife blade slides adjacent to the center V arms, as shown in FIG. 27, to cut the suture. FIG. 27 also illustrates the knife blade 392 which is seated in a positioning slot 436 between a blade mounting structure 432 and a removable blade cap 434 which is secured to the blade mounting structure 432 by a removable screw 436.

Off Load Dial Assembly For Needles and Sutures

The offload station 500 is more particularly illustrated and described with respect to FIGS. 17 and 18–18(b) in which a plurality of needle buckets 502 are circumferentially arranged on a rotatable turntable 504 to be indexed under the collection point 506 defined by an intercept axis of a needle stripper 190 and the face of the universal gripper 155. As the needles are stripped from the universal gripper, they fall into a needle collection bucket which collects the needle inside the bucket, and most of the suture outside the bucket.

One needle stripper assembly 190 is illustrated in FIG. 21, which stripper includes a reciprocating stripping pin 192, which is spring biased inwardly by spring 193, and reciprocated outwardly by pneumatic motor 194 to engage the needle to be stripped. The stripping assemblies are secured in position by means of a bracket 191 which is bolted to the frame of the apparatus.

The present invention includes a pair of needle strippers 190a,190b, the locations of which are illustrated in FIG. 14(a) adjacent the circumference of the swage dial plate 110. Needle stripper assemblies 190(a), (b) are mounted to the frame of the stand alone swage machine by means of brackets 191a,191b to provide a longitudinal axis of reciprocation for the needle stripping pins 192a,b that is tangential to the circumference described by the face of the universal grippers 155. When the needle stripper pins 192 are retracted, as illustrated in FIG. 21, the universal gripper passes the needle stripping station without engagement. However, when the needle stripping pins are reciprocated outwardly, they intercept the path of needle 39 and are positioned to reciprocate into a space 188 (illustrated in FIGS. 14(b) and 15) defined between the face of the universal gripper 155 and the needle 39. Simultaneously therewith, the plunger 170 on the universal gripper is depressed by one of the offload cams 172 to open the jaws 146,148 of the universal gripper and enable the needle to be stripped from the universal gripper.

One needle stripper is used at the pull test station to remove needles that have failed the suture pull test, and a second is used at the off load station to insure a positive removal of the needle and suture assembly from the universal gripper at the off load station.

The needle stripper assembly 190(a) illustrated in FIG. 14(a) is used to remove needles that have failed the pull test at the pull test station 400. The needle stripper assembly 190(b) is used to remove the needle and suture assembly from the universal gripper for bundling in the offload station 500.

The needle bucket of the present invention is illustrated in FIGS. 18–18(b), wherein FIG. 22 is a side view illustrating the a side view of the bucket and the radial reciprocation of the needle bucket, with FIG. 22 (a) illustrating a front view of the bucket and FIG. 22(b) illustrating a top view of the bucket.

Figure 20:
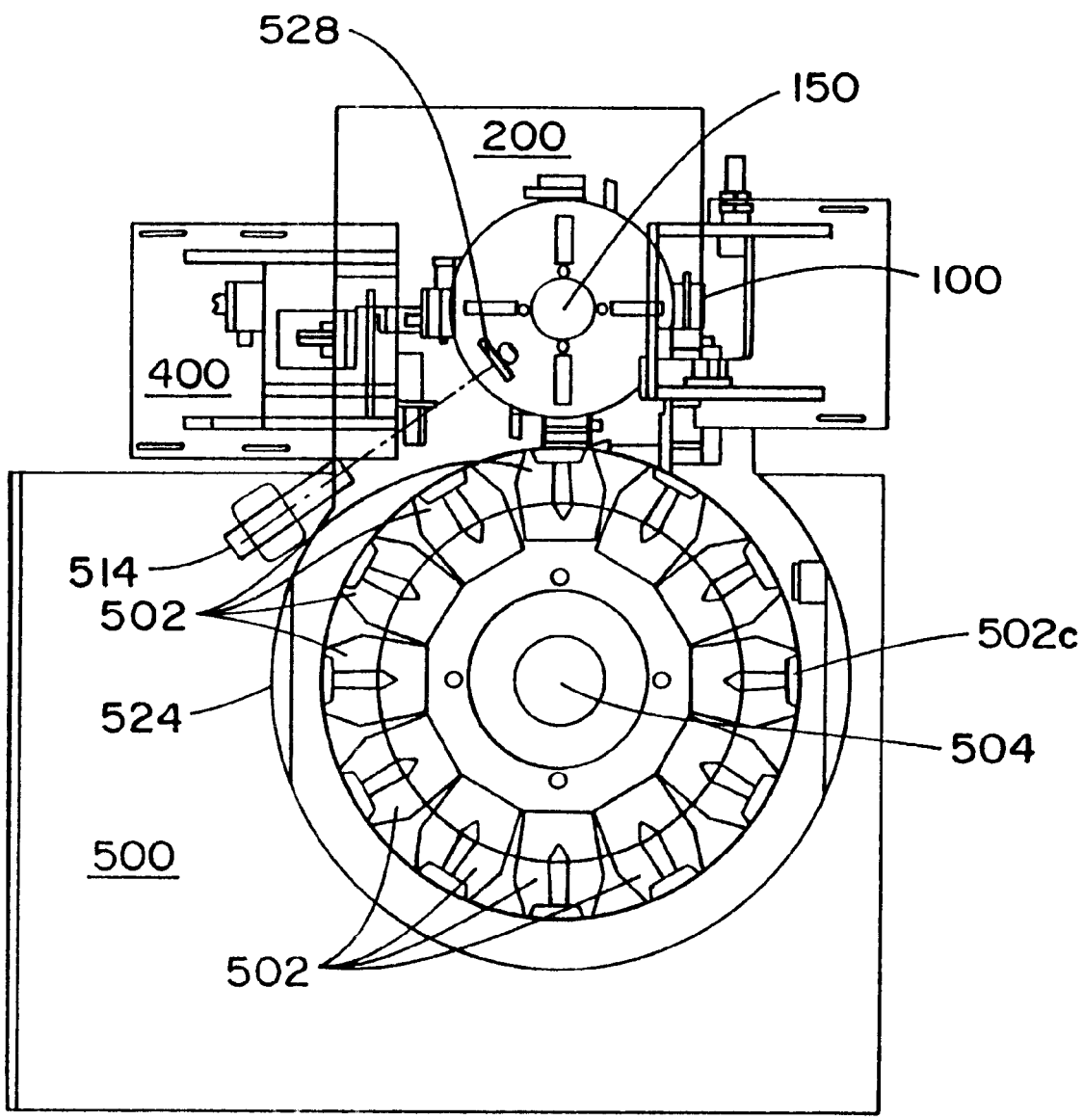
FIG. 20 is a top plan view of the needle bundling station of the present invention illustrating a plurality of compartments, each of which receives a predetermined number of needle and suture assemblies.

As illustrated in FIG. 22, dotted line axis A illustrates the circumferential path of the needle in a horizontal plane, while carried by the universal gripper, while axis B and C illustrate the the radial reciprocation of the universal gripper 155 mounted on the swage dial. The needle stripping pin 192b engages the needle at the intersection of axis A and C at intersect 506 causing the needle to drop into the needle bucket 502. The needle falls into the bucket with the suture draped over a comb-like face 520 which holds the suture and assists in preventing entanglement of the sutures when they are removed from the needle bucket. Most of the suture remains outside the bucket, and is captured within a suture shroud 524, illustrated in FIG. 20. The suture shroud 524 guides the unsupported end of the suture and prevents entanglement with the moving parts of the apparatus below the circumferential path described by the universal gripper. In addition, a stream of deionized air may be provided at this station to assist in the orderly collection of the sutures following the swage assembly.

Each of the needle buckets includes a second comb-like surface 522 on one side of the bucket, and an upstanding extended wall portion 526 on the far side of the collection bucket to assist in capturing any late dropping needles.

Each of the needle buckets 502 is spring mounted for radial reciprocation on turntable 504 by means of a spring loaded reciprocating mount 508 which nominally biases the needle bucket 502 inwardly. When the needle bucket has arrived at the offload position, the bucket 502 is reciprocated outwardly as illustrated in FIG. 22 by a pneumatic motor 510 to the position 502b illustrated in FIG. 22.

FIG. 17 also illustrates a detector 514 which is focused on a reflector plate 528 under the swage dial assembly 150 that is triggered by a passing suture to actuate the needle stripping assembly 190(b).

After a predetermined number of needle and suture assemblies have been collected in the needle bucket 502, the needle bucket 502 is reciprocated inwardly by relaxing air motor 510 and the turntable 504 is indexed to position the next available needle bucket 502 under the off load station. While 12 offload buckets 502 have been illustrated in FIG. 17(a), it is understood that a smaller number of buckets could be used if desired.

After a needle bucket 502 has been filled with a predetermined number of needle and suture assemblies, and rotated to the position illustrated at 502(c) in FIG. 17, the bundle of needle and suture assemblies may be removed for subsequent handling and packaging.

As is readily apparent to one skilled in the art, many variations on the above described embodiment are possible. The foregoing description is exemplary only and not to be construed as limiting the scope of the invention, which is defined in the claims, as follows.

What is claimed:

1. A needle threading and swaging apparatus for attaching a single suture to either a single suture or a pair of surgical needles, each needle having a suture receiving opening formed therein, said apparatus comprising:

(a) at least two universal grippers, each gripper sequentially receiving a first surgical needle and indexing said first surgical needle in a predetermined orientation from a first predetermined location through a swage station, (b) a suture cutting and inserting station located at a second predetermined location for automatically cutting an indefinite length of suture material to a definite length, said definite length having a first end and a second end, said suture cutting and inserting station having a first gripper for inserting a first end of said suture into the suture receiving opening formed in the first surgical needle, and a second invertible gripper for gripping the indefinite length suture, and after the suture has been cut, automatically inserting said suture into said suture receiving opening formed in a second surgical needle;

(c) a rotatable carriage for said second invertible gripper, to rotate said second gripper and invert a cut end of said suture for insertion into said second surgical needle in the event double-armed sutures are to be formed;

(d) a swage station for sequentially swaging each surgical needle to close the suture receiving openings of each surgical needle about a definite length of suture, wherein the first needle is secured to the first end of said definite length of suture and the second needle to the second end of said definite length of suture when a double-armed needle and suture assembly is to be formed.

2. The needle threading and swaging apparatus according to claim 1 wherein said second invertible gripper includes a motor for rotating the rotatable carriage and gripper after the suture has been cut from said indefinite length when a double-armed suture is to be formed.

3. The needle threading and swaging apparatus according to claim 1, wherein the suture cutting and inserting station located at said second predetermined location further comprises:

(a) a drawing frame, said frame having a first and a second longitudinal member and defining a drawing axis parallel thereto;

(b) means for feeding a flexible indefinite length suture strand to said drawing axis for drawing and cutting;

(c) said first gripper and said second invertible gripper mounted for reciprocal movement on said first and said second longitudinal members respectively;

(d) a cutter assembly for cutting said indefinite length suture strand.

4. The needle threading and swaging apparatus according to claim 3, wherein the second invertible gripper is reciprocated to a start position along said drawing axis above said cutter assembly, while said first gripper is drawing said indefinite length suture strand to an insertion zone located a predetermined distance beyond said cutter assembly when a double-armed suture is to be formed.

5. The needle threading and swaging apparatus according to claim 4, wherein during the formation of a double-armed suture, said second invertible gripper inverts a second end of said definite length suture and reciprocates it to an insert position along said drawing axis above said cutter assembly to enable the second end of said cut suture strand to be inserted within said suture receiving opening of said second surgical needle for swaging thereto.

6. The needle threading and swaging apparatus according to claim 3, wherein the suture cutting and inserting station located at said second predetermined location further comprises first and second drive motors for enabling reciprocal movement of respective first and second grippers.

7. The needle threading and swaging apparatus according to claim 6 wherein the apparatus further comprises a computer control means for said invertible gripper, said cutter assembly and said first and second drive motors to selectively form single armed sutures or double-armed sutures from said indefinite length of suture.

8. The needle threading and swaging apparatus according to claim 7 wherein the apparatus further comprises a moveable carrier mounted for selective movement along said drawing axis, said movable carrier having said cutter assembly mounted thereon.

9. The needle threading and swaging apparatus according to claim 8 wherein the suture cutting and inserting station further includes means for tensioning said indefinite length suture during at least the drawing and cutting thereof.

10. A needle threading and swaging apparatus for attaching a suture to a pair of surgical needles, each needle having a suture receiving opening formed therein to form a double-armed suture, said apparatus comprising:

(a) at least a first and a second universal gripper for sequentially receiving a first and a second surgical needle of said pair at a first predetermined location and transferring said needles in a predetermined orientation to a swaging station;

(b) a suture drawing and cutting station for automatically cutting an indefinite length of suture material to a definite length and automatically inserting a first end of said definite length suture into said suture receiving opening formed in the first surgical needle and automatically inverting and inserting a second end of said definite length suture into said suture receiving opening formed in the second surgical needle after the indefinite length of suture has been cut;

(c) a swage station for sequentially swaging the first and the second of said pair of surgical needles to close the respective suture receiving openings in the first and the second surgical needles about the first and second ends of said definite length suture to secure said suture thereto and form therefrom a double-armed needle and suture assembly;

whereby surgical needles and an indefinite length of suture material are formed into a plurality of double-armed surgical needle and suture assemblies.

11. A needle threading and swaging apparatus for attaching a suture to a pair of surgical needles as claimed in claim 10, wherein said apparatus further comprises a cutter assembly for cutting said indefinite length suture to a definite length, and means for tensioning said indefinite length suture during at least the drawing and cutting thereof.

12. A needle threading and swaging apparatus for attaching a suture to a pair of surgical needles to form a double armed suture wherein said apparatus further comprises:

(a) a cutter assembly for cutting said indefinite length suture to a definite length, (b) means for tensioning said indefinite length suture during at least the drawing and cutting thereof, (c) first and second grippers having retractable gripping elements having a first engaged position and a second retracted position, wherein one of said first and second grippers traverses the drawing axis on a draw stroke with gripping elements engaged, and the other of said first and second grippers reciprocates along the same axis with the gripping elements retracted to avoid mechanical interference therewith, at least one of said grippers being an invertible gripper which enables swaging of said indefinite length suture to a pair of needles to form a double armed suture.

13. The needle threading and swaging apparatus according to claim 11 wherein the suture drawing and cutting station further includes a tipping station for heat treating a portion of said indefinite length strand of suture material while under tension at to form a treated portion of said indefinite length strand.

14. The needle threading and swaging apparatus according to claim 13 wherein at least one of said tipping station or said cutter assembly is mounted on a movable carrier to enable said cutter assembly to cut a plurality of definite lengths of sutures from said indefinite length, with each cut occurring in a treated zone on said indefinite length of suture.

15. The needle threading and swaging apparatus according to claim 14 wherein said indefinite length strand is supported at a free end adjacent an insertion position by said first gripper while said tipping station is heating a portion of said strand at a treatment zone remote from said insertion position and said cutter assembly.

16. The needle threading and swaging apparatus according to claim 15 wherein said cutter assembly cuts said indefinite length suture in a treated portion remote from said treatment zone to create a suture strand of definite length supported at the first end by said first needle, and at said second end by said second gripper.

17. The needle threading and swaging apparatus according to claim 11 wherein said cutter assembly includes a retractable cutter having a cutting blade mounted for at least reciprocal movement transverse to a first axis defined by said indefinite length strand from a first retracted position to a second cutting position and a suture support for accurately positioning said indefinite length strand of suture material for cutting thereof, and for supporting said strand as the cutting blade traverses said first axis as it reciprocates from said retracted position to said cutting position.

18. The needle threading and swaging apparatus according to claim 11, wherein the suture drawing and cutting station further comprises a drawing frame which defines a drawing axis and a means for feeding a flexible indefinite length suture strand to said drawing axis for drawing and cutting, wherein said first gripper and second invertible gripper are mounted for reciprocal movement on either side of said drawing axis.

19. The needle threading and swaging apparatus according to claim 18, wherein the second invertible gripper is reciprocal to a start position along said drawing axis above said cutter assembly, while said first gripper is drawing said indefinite length suture strand to an insertion zone located a predetermined distance beyond said cutter assembly, whereby said indefinite length suture strand is inserted within said suture receiving opening of the first of said pair of needles and cut to a predetermined length by said cutter assembly after said first needle has been swaged.

20. The needle threading and swaging apparatus according to claim 19, wherein said second invertible gripper inverts a second end of said definite length suture and reciprocates it to an insert position along said drawing axis above said cutter assembly to enable the second end of said cut suture strand to be inserted within said suture receiving opening of the second of said pair of needles for swaging thereto.

21. A method of forming a double-armed suture, wherein the suture is swaged to a pair of surgical needles, said method comprising:

(a) sequentially positioning a first and then a second surgical needle in a predetermined position in a swage station for subsequent sequential swaging;

(b) automatically inserting and swaging a first end of an indefinite length of suture material into a suture receiving opening in the first of said needles, thereby drawing said indefinite length to a definite length, said definite length having a first end and a second end;

(c) cutting said definite length of suture from said indefinite length of suture material along a cut axis;

(d) inverting the second end of said definite length of suture, and automatically inserting and swaging second end of said indefinite length of suture material into a suture receiving opening in the second of said needles to thereby form a double-armed suture assembly.

22. A method of forming a double-armed suture as claimed in claim 21 which further includes the step of rotating an invertible gripper to invert the second end of said definite length of suture material to enable insertion into the second of said needles.

23. A method of forming a double-armed suture as claimed in claim 21 which further includes the steps of:

(a) feeding a flexible indefinite length suture strand along a drawing axis for drawing and cutting;

(b) reciprocating a first gripper and a second invertible gripper on either side of said drawing axis, wherein said first gripper draws said indefinite length suture strand to an insertion position located a predetermined distance beyond a suture cutter assembly while said second invertible gripper is reciprocated to a start position along said drawing axis above said cutter assembly; and then (c) performing the swaging step (b) and then the cutting step (c) of claim 21.

24. A method of forming a double-armed suture as claimed in claim 23 wherein said inverting step includes the step of gripping the second end of said definite length of suture with said invertible gripper, rotating the gripper, and reciprocating it to an insert position along said drawing axis above said cutter assembly to enable the second end of said cut suture strand to be inserted within said suture receiving opening of the second of said pair of needles, and then swaging said second needles.

25. A method of forming a double-armed suture as claimed in claim 24, which further includes the step of tensioning said indefinite length suture during at least the drawing and cutting thereof.

26. A method of forming a double-armed suture as claimed in claim 21, which further includes the step of heating a portion of said strand at a heat treatment zone remote from said cut axis.

27. A method of forming a double-armed suture as claimed in claim 26 which further includes the steps of reciprocating a tipping station which heats the suture and a cutter assembly which cuts the suture along the drawing axis to enable said cutter assembly to cut a plurality of definite lengths of sutures from said indefinite length of suture, with each cut occurring in a treated zone on said indefinite length of suture.

28. A method of forming a double-armed suture as claimed in claim 27 which further includes the step of supporting said indefinite length strand at a free end adjacent the first of said surgical needles with a first gripper while said tipping station is heating a portion of said indefinite length strand at a treatment zone remote from said cutter assembly.

29. A method of forming a double-armed suture as claimed in claim 27 wherein said cutter assembly cuts said indefinite length suture in a treated portion remote from said treatment zone to create a suture strand of definite length supported at the first end by said first needle, and at said second end by said second invertible gripper.

30. A method of forming a double-armed suture as claimed in claim 26 which further includes the step of cooling the suture after said heating step and before said cutting step.

\* \* \* \* \*